(12) United States Patent
Carruth et al.

(10) Patent No.: US 11,793,554 B2
(45) Date of Patent: Oct. 24, 2023

(54) TANDEM ROD CONNECTORS AND RELATED METHODS

(71) Applicant: Medos International Sarl, Le Locle (CH)

(72) Inventors: Robert Carruth, North Attleboro, MA (US); John Dieselman, Raynham, MA (US); Kevin Lee, Canton, MA (US); J. Riley Hawkins, Cumberland, RI (US)

(73) Assignee: Medos International Sarl, Le Locle (CH)

( * ) Notice: Subject to any disclaimer, the term of this patent is extended or adjusted under 35 U.S.C. 154(b) by 325 days.

(21) Appl. No.: 16/951,585

(22) Filed: Nov. 18, 2020

(65) Prior Publication Data

US 2021/0068872 A1   Mar. 11, 2021

Related U.S. Application Data

(63) Continuation of application No. 16/280,918, filed on Feb. 20, 2019, now Pat. No. 10,869,695, which is a
(Continued)

(51) Int. Cl.
*A61B 17/70* (2006.01)
*A61B 17/86* (2006.01)

(52) U.S. Cl.
CPC ...... *A61B 17/7049* (2013.01); *A61B 17/7001* (2013.01); *A61B 17/7032* (2013.01);
(Continued)

(58) Field of Classification Search
CPC ................ A61B 17/70; A61B 17/7023; A61B 17/7049–7052
See application file for complete search history.

(56) References Cited

U.S. PATENT DOCUMENTS 5,261,909 A   11/1993   Sutterlin et al.
5,312,405 A   5/1994    Korotko et al.
(Continued)

FOREIGN PATENT DOCUMENTS

CN   101198284 A   6/2008
CN   201194833 Y   2/2009
(Continued)

OTHER PUBLICATIONS

U.S. Appl. No. 15/158,127, filed May 18, 2016, Implant Connectors and Related Methods.
(Continued)

*Primary Examiner* — Eduardo C Robert
*Assistant Examiner* — Michelle C Eckman
(74) *Attorney, Agent, or Firm* — Barnes & Thornburg LLP

(57) ABSTRACT

Connectors are disclosed herein that can be used to attach a rod to a bone anchor assembly that is already occupied by a separate rod. Various ways of attaching the connector to the bone anchor assembly are disclosed, including arrangements in which the connector is locked to the bone anchor, arrangements in which the connector is constrained in one or more degrees of freedom relative to the bone anchor, arrangements in which the connector is adjustable in one or more degrees of freedom relative to the bone anchor, and arrangements that include a spherical articulation joint. In some embodiments, attachment of the connector to a bone anchor can be aided with the use of a positioner. The geometry of the connector can be selected to minimize the offset between a first rod received in the bone anchor assembly and a second rod received in the connector, for example using an angled or curved rod recess and/or a fastener, or set screw, that is offset from the center of the rod or angled relative to the bone anchor. The connector can be configured to align the
(Continued)

first and second rods in a common coronal plane, or can be configured to position one rod more anterior or posterior than the other rod.

21 Claims, 28 Drawing Sheets

Related U.S. Application Data continuation of application No. 15/430,188, filed on Feb. 10, 2017, now Pat. No. 10,238,432.

(52) U.S. Cl.
 CPC ........ *A61B 17/8605* (2013.01); *A61B 17/866* (2013.01); *A61B 17/8685* (2013.01)

(56) References Cited

U.S. PATENT DOCUMENTS

| | | | |
|---|---|---|---|
| 5,569,246 | A | 10/1996 | Ojima et al. |
| 5,613,968 | A * | 3/1997 | Lin .................... A61B 17/7037 606/301 |
| 5,667,506 | A | 9/1997 | Sutterlin |
| 5,669,910 | A | 9/1997 | Korhonen et al. |
| 5,709,685 | A | 1/1998 | Dombrowski et al. |
| 5,716,355 | A | 2/1998 | Jackson et al. |
| 5,725,528 | A | 3/1998 | Errico et al. |
| 5,769,857 | A | 6/1998 | Reztzov et al. |
| 5,776,135 | A | 7/1998 | Errico et al. |
| 5,876,403 | A | 3/1999 | Shitoto |
| 5,885,284 | A | 3/1999 | Errico et al. |
| 5,980,523 | A | 11/1999 | Jackson |
| 6,050,997 | A | 4/2000 | Mullane |
| 6,083,226 | A | 7/2000 | Fiz |
| 6,096,039 | A | 8/2000 | Stoltenberg et al. |
| 6,231,575 | B1 | 5/2001 | Krag |
| 6,238,396 | B1 | 5/2001 | Lombardo |
| 6,248,104 | B1 * | 6/2001 | Chopin .............. A61B 17/7041 606/267 |
| 6,280,443 | B1 | 8/2001 | Gu et al. |
| 6,309,390 | B1 | 10/2001 | Le Couedic et al. |
| 6,328,739 | B1 | 12/2001 | Liu et al. |
| 6,328,740 | B1 | 12/2001 | Richelsoph |
| 6,402,751 | B1 | 6/2002 | Hoeck et al. |
| 6,468,276 | B1 | 10/2002 | McKay |
| 6,478,798 | B1 | 11/2002 | Howland |
| 6,524,310 | B1 | 2/2003 | Lombardo et al. |
| 6,551,318 | B1 | 4/2003 | Stahurski |
| 6,554,832 | B2 | 4/2003 | Shluzas |
| 6,592,585 | B2 | 7/2003 | Lee et al. |
| 6,616,668 | B2 | 9/2003 | Altarac et al. |
| 6,676,661 | B1 | 1/2004 | Martin Benlloch et al. |
| 6,736,775 | B2 | 5/2004 | Phillips |
| 6,736,820 | B2 | 5/2004 | Biedermann et al. |
| 6,783,526 | B1 | 8/2004 | Lin et al. |
| 6,786,907 | B2 | 9/2004 | Lange |
| 6,793,657 | B2 | 9/2004 | Lee et al. |
| 6,974,460 | B2 | 12/2005 | Carbone et al. |
| 7,029,474 | B2 | 4/2006 | Richelsoph et al. |
| 7,104,993 | B2 | 9/2006 | Baynham et al. |
| 7,122,036 | B2 | 10/2006 | Vanacker |
| 7,163,538 | B2 | 1/2007 | Altarac et al. |
| 7,166,108 | B2 | 1/2007 | Mazda et al. |
| 7,179,261 | B2 | 2/2007 | Sicvol et al. |
| 7,189,236 | B2 | 3/2007 | Taylor et al. |
| 7,485,132 | B1 | 2/2009 | McBride et al. |
| 7,572,277 | B2 | 8/2009 | Roussouly et al. |
| 7,575,587 | B2 | 8/2009 | Rezach et al. |
| 7,585,314 | B2 | 9/2009 | Taylor et al. |
| 7,628,799 | B2 | 12/2009 | Richelsoph et al. |
| 7,666,210 | B2 | 2/2010 | Franck et al. |
| 7,704,270 | B2 | 4/2010 | De Coninck |
| 7,717,938 | B2 | 5/2010 | Kim et al. |
| 7,717,940 | B2 | 5/2010 | Woods et al. |
| 7,744,632 | B2 | 6/2010 | Usher |
| 7,744,634 | B2 | 6/2010 | Farris |
| 7,753,940 | B2 | 7/2010 | Veldman et al. |
| 7,771,474 | B2 | 8/2010 | Cordaro |
| 7,789,897 | B2 | 9/2010 | Sanders |
| 7,794,478 | B2 | 9/2010 | Nilsson |
| 7,803,174 | B2 | 9/2010 | Denis et al. |
| 7,806,912 | B2 | 10/2010 | Lawton et al. |
| 7,833,248 | B2 | 11/2010 | Markworth et al. |
| 7,837,714 | B2 | 11/2010 | Drewry et al. |
| 7,842,071 | B2 | 11/2010 | Hawkes |
| 7,901,434 | B2 | 3/2011 | Drewry et al. |
| 7,909,854 | B2 | 3/2011 | Schwab |
| 7,922,746 | B2 | 4/2011 | Miller |
| 7,922,747 | B2 | 4/2011 | Kirschman |
| 7,927,355 | B2 | 4/2011 | Berrevoets et al. |
| 7,942,901 | B2 | 5/2011 | Rezach |
| 7,947,066 | B2 | 5/2011 | Tepper et al. |
| 7,959,653 | B2 | 6/2011 | Thramann et al. |
| 7,993,371 | B2 | 8/2011 | Farris |
| 8,016,862 | B2 | 9/2011 | Felix et al. |
| 8,025,679 | B2 | 9/2011 | Nichols et al. |
| 8,062,338 | B2 | 11/2011 | McBride et al. |
| 8,075,594 | B2 | 12/2011 | Purcell |
| 8,080,037 | B2 | 12/2011 | Butler et al. |
| 8,097,022 | B2 | 1/2012 | Marik |
| 8,109,974 | B2 | 2/2012 | Boomer et al. |
| 8,114,133 | B2 | 2/2012 | Logan |
| 8,147,519 | B2 | 4/2012 | Wilcox |
| 8,152,851 | B2 | 4/2012 | Mueller et al. |
| 8,167,908 | B2 | 5/2012 | Ely et al. |
| 8,172,879 | B2 | 5/2012 | Butler et al. |
| 8,192,467 | B2 | 6/2012 | Felix et al. |
| 8,197,515 | B2 | 6/2012 | Levy et al. |
| 8,236,028 | B2 | 8/2012 | Kalfas et al. |
| 8,241,334 | B2 | 8/2012 | Butler et al. |
| 8,246,657 | B1 | 8/2012 | Samuel |
| 8,246,665 | B2 | 8/2012 | Butler et al. |
| 8,262,700 | B2 | 9/2012 | Cho et al. |
| 8,262,701 | B2 | 9/2012 | Rathbun et al. |
| 8,292,924 | B2 | 10/2012 | Neary et al. |
| 8,298,266 | B2 | 10/2012 | Miller |
| 8,298,269 | B2 | 10/2012 | Null et al. |
| 8,317,837 | B2 | 11/2012 | Rezach et al. |
| 8,337,527 | B2 | 12/2012 | Hawkins et al. |
| 8,337,532 | B1 | 12/2012 | McLean et al. |
| 8,366,749 | B2 | 2/2013 | Sweeney |
| 8,366,750 | B2 | 2/2013 | Iott et al. |
| 8,414,616 | B2 | 4/2013 | Berrevoets et al. |
| 8,414,617 | B2 | 4/2013 | Young et al. |
| 8,419,771 | B2 | 4/2013 | Poirier et al. |
| 8,419,773 | B2 | 4/2013 | Biedermann et al. |
| 8,430,916 | B1 | 4/2013 | Winslow et al. |
| 8,460,342 | B2 | 6/2013 | Courtney et al. |
| 8,470,001 | B2 | 6/2013 | Trautwein et al. |
| 8,591,550 | B2 | 11/2013 | Ludwig et al. |
| 8,617,213 | B2 | 12/2013 | Moore et al. |
| 8,628,559 | B2 | 1/2014 | Iott et al. |
| 8,641,739 | B2 | 2/2014 | McLean et al. |
| 8,657,856 | B2 | 2/2014 | Gephart et al. |
| 8,668,721 | B2 | 3/2014 | Miller |
| 8,715,323 | B2 | 5/2014 | Ballard et al. |
| 8,721,689 | B2 | 5/2014 | Butler et al. |
| 8,728,124 | B2 | 5/2014 | Miller |
| 8,758,411 | B1 | 6/2014 | Rayon et al. |
| 8,771,319 | B2 | 7/2014 | Prajapati |
| 8,808,332 | B2 | 8/2014 | Iott et al. |
| 8,828,056 | B2 | 9/2014 | Buss et al. |
| 8,864,798 | B2 | 10/2014 | Weiman et al. |
| 8,864,799 | B2 | 10/2014 | Kraus |
| 8,870,923 | B2 | 10/2014 | Richelsoph |
| 8,882,803 | B2 | 11/2014 | Iott et al. |
| 8,888,777 | B2 | 11/2014 | Mullaney |
| 8,888,819 | B2 | 11/2014 | Frasier et al. |
| 8,920,471 | B2 | 12/2014 | Barrus et al. |
| 8,920,475 | B1 | 12/2014 | Ziemek et al. |
| 8,945,186 | B2 | 2/2015 | Walker et al. |
| 8,951,289 | B2 | 2/2015 | Matityahu |
| 8,998,956 | B2 | 4/2015 | George et al. |

(56) References Cited

U.S. PATENT DOCUMENTS

| | | |
|---|---|---|
| 8,998,961 B1 | 4/2015 | Ziemek et al. |
| 9,005,249 B2 | 4/2015 | Rinner et al. |
| 9,023,087 B2 | 5/2015 | Frankel et al. |
| 9,055,980 B2 | 6/2015 | Biedermann |
| 9,060,815 B1 | 6/2015 | Gustine et al. |
| 9,072,547 B2 | 7/2015 | Harper et al. |
| 9,084,630 B2 | 7/2015 | Mullaney |
| 9,095,380 B2 | 8/2015 | Mir et al. |
| 9,101,400 B2 | 8/2015 | Trieu et al. |
| 9,101,405 B2 | 8/2015 | Dickinson et al. |
| 9,107,703 B2 | 8/2015 | Torres |
| 9,113,961 B2 | 8/2015 | Larroque-Lahitette |
| 9,119,675 B2 | 9/2015 | Lee et al. |
| 9,125,691 B2 | 9/2015 | Gunn |
| 9,131,963 B2 | 9/2015 | Predick |
| 9,131,964 B2 | 9/2015 | Blain et al. |
| 9,149,301 B2 | 10/2015 | Asaad et al. |
| 9,155,565 B2 | 10/2015 | Boomer et al. |
| 9,155,580 B2 | 10/2015 | Cormier et al. |
| 9,186,184 B2 | 11/2015 | Janowski |
| 9,198,696 B1 | 12/2015 | Bannigan et al. |
| 9,204,901 B2 | 12/2015 | Black et al. |
| 9,220,541 B1 | 12/2015 | Dant et al. |
| 9,247,964 B1* | 2/2016 | Shoshtaev .......... A61B 17/7083 |
| 9,265,548 B2 | 2/2016 | Jones et al. |
| 9,271,763 B2 | 3/2016 | Barrus et al. |
| 9,339,307 B2 | 5/2016 | McClintock et al. |
| 9,345,521 B2 | 5/2016 | Ziolo |
| 9,421,041 B2 | 8/2016 | Richelsoph |
| 9,433,445 B2 | 9/2016 | Ramsay et al. |
| 9,451,994 B1 | 9/2016 | Whipple et al. |
| 9,474,554 B2 | 10/2016 | Strnad |
| 9,517,089 B1 | 12/2016 | Casey et al. |
| 9,561,058 B2 | 2/2017 | Lange et al. |
| 9,579,126 B2 | 2/2017 | Zhang et al. |
| 9,615,867 B2 | 4/2017 | Picetti et al. |
| 9,629,663 B2 | 4/2017 | Ludwig et al. |
| 9,649,136 B2 | 5/2017 | George et al. |
| 9,693,808 B2 | 7/2017 | Fauth et al. |
| 9,724,131 B2 | 8/2017 | Bootwala et al. |
| 9,770,269 B1* | 9/2017 | Shoshtaev .......... A61B 17/7049 |
| 9,956,009 B1 | 5/2018 | Shoshtaev |
| 10,238,432 B2 | 3/2019 | Carruth et al. |
| 10,321,939 B2 | 6/2019 | Lee et al. |
| 10,398,476 B2 | 9/2019 | Lee et al. |
| 10,492,835 B2 | 12/2019 | Lee et al. |
| 10,517,647 B2 | 12/2019 | Lee et al. |
| 10,561,454 B2 | 2/2020 | Lee et al. |
| 10,869,695 B2 | 12/2020 | Carruth et al. |
| 10,966,761 B2 | 4/2021 | Lee et al. |
| 11,058,463 B2 | 7/2021 | Lee et al. |
| 11,076,890 B2 | 8/2021 | Ortiz et al. |
| 11,160,583 B2 | 11/2021 | Lee et al. |
| 11,382,676 B2 | 7/2022 | Lee et al. |
| 2002/0032442 A1 | 3/2002 | Altarac et al. |
| 2002/0042614 A1 | 4/2002 | Ueyama et al. |
| 2003/0045878 A1 | 3/2003 | Petit et al. |
| 2003/0045879 A1 | 3/2003 | Minfelde et al. |
| 2003/0153914 A1 | 8/2003 | Oribe et al. |
| 2004/0111088 A1 | 6/2004 | Picetti et al. |
| 2004/0147929 A1 | 7/2004 | Biedermann et al. |
| 2004/0162558 A1 | 8/2004 | Hegde et al. |
| 2005/0131404 A1 | 6/2005 | Mazda et al. |
| 2005/0149019 A1 | 7/2005 | Sasing et al. |
| 2005/0171537 A1 | 8/2005 | Mazel et al. |
| 2005/0228326 A1 | 10/2005 | Kalfas et al. |
| 2005/0228377 A1 | 10/2005 | Chao et al. |
| 2005/0228378 A1 | 10/2005 | Kalfas et al. |
| 2005/0228382 A1 | 10/2005 | Richelsoph et al. |
| 2006/0039750 A1 | 2/2006 | Thomke et al. |
| 2006/0058789 A1 | 3/2006 | Kim et al. |
| 2006/0064090 A1 | 3/2006 | Park |
| 2006/0064091 A1* | 3/2006 | Ludwig ................ A61B 17/701 606/279 |
| 2006/0079892 A1 | 4/2006 | Roychowdhury et al. |
| 2006/0177263 A1 | 8/2006 | Thomke et al. |
| 2006/0195096 A1 | 8/2006 | Lee et al. |
| 2006/0206114 A1 | 9/2006 | Ensign et al. |
| 2006/0229611 A1 | 10/2006 | Avery et al. |
| 2006/0241598 A1 | 10/2006 | Khalili |
| 2006/0282074 A1 | 12/2006 | Renaud et al. |
| 2007/0049932 A1 | 3/2007 | Richelsoph et al. |
| 2007/0100339 A1 | 5/2007 | Clement et al. |
| 2007/0123860 A1 | 5/2007 | Francis et al. |
| 2007/0173825 A1 | 7/2007 | Sharifi-Mehr et al. |
| 2007/0173829 A1 | 7/2007 | Drewry et al. |
| 2007/0233062 A1 | 10/2007 | Berry |
| 2007/0233090 A1 | 10/2007 | Naifeh et al. |
| 2007/0250061 A1 | 10/2007 | Chin et al. |
| 2007/0270805 A1 | 11/2007 | Miller et al. |
| 2007/0270817 A1 | 11/2007 | Rezach |
| 2007/0270818 A1 | 11/2007 | Rezach |
| 2007/0276384 A1 | 11/2007 | Spratt |
| 2008/0021466 A1 | 1/2008 | Shadduck et al. |
| 2008/0045963 A1 | 2/2008 | Abdou |
| 2008/0058805 A1 | 3/2008 | Stuart |
| 2008/0082112 A1 | 4/2008 | Lawton et al. |
| 2008/0109039 A1 | 5/2008 | Michielli et al. |
| 2008/0177318 A1 | 7/2008 | Veldman et al. |
| 2008/0177323 A1 | 7/2008 | Null et al. |
| 2008/0195150 A1* | 8/2008 | Bishop ............... A61B 17/7037 606/301 |
| 2008/0234743 A1 | 9/2008 | Marik |
| 2008/0255617 A1 | 10/2008 | Cho et al. |
| 2008/0262552 A1 | 10/2008 | Kim |
| 2008/0262553 A1 | 10/2008 | Hawkins et al. |
| 2008/0269810 A1 | 10/2008 | Zhang et al. |
| 2008/0281361 A1 | 11/2008 | Vittur et al. |
| 2009/0036929 A1 | 2/2009 | Reglos et al. |
| 2009/0082812 A1 | 3/2009 | Lewis |
| 2009/0105765 A1 | 4/2009 | Strnad |
| 2009/0157120 A1 | 6/2009 | Marino et al. |
| 2009/0163956 A1 | 6/2009 | Biedermann et al. |
| 2009/0187217 A1 | 7/2009 | Weiman et al. |
| 2009/0204153 A1 | 8/2009 | Suzuki et al. |
| 2009/0222042 A1 | 9/2009 | Firkins et al. |
| 2009/0228046 A1 | 9/2009 | Garamszegi |
| 2009/0249851 A1 | 10/2009 | Isaacs |
| 2010/0004686 A1 | 1/2010 | Lemoine |
| 2010/0004693 A1 | 1/2010 | Miller et al. |
| 2010/0010545 A1 | 1/2010 | Park et al. |
| 2010/0087864 A1 | 4/2010 | Klein et al. |
| 2010/0087867 A1 | 4/2010 | Klein et al. |
| 2010/0094345 A1* | 4/2010 | Saidha ............... A61B 17/7052 606/250 |
| 2010/0094346 A1 | 4/2010 | Matityahu |
| 2010/0094349 A1 | 4/2010 | Hammer et al. |
| 2010/0114165 A1 | 5/2010 | Ely |
| 2010/0114167 A1 | 5/2010 | Wilcox et al. |
| 2010/0160981 A1* | 6/2010 | Butler ................ A61B 17/7049 606/308 |
| 2010/0204733 A1* | 8/2010 | Rathbun ............ A61B 17/7049 606/251 |
| 2010/0241171 A1 | 9/2010 | Clement et al. |
| 2010/0274286 A1 | 10/2010 | Blain et al. |
| 2010/0280552 A1 | 11/2010 | Lee |
| 2010/0298884 A1 | 11/2010 | Faizan et al. |
| 2010/0324599 A1* | 12/2010 | Montello ........... A61B 17/7032 606/279 |
| 2011/0034957 A1 | 2/2011 | Biedermann |
| 2011/0046675 A1 | 2/2011 | Barrus et al. |
| 2011/0066187 A1 | 3/2011 | Fang et al. |
| 2011/0087287 A1 | 4/2011 | Reeder, Jr. et al. |
| 2011/0087288 A1 | 4/2011 | Stevenson et al. |
| 2011/0098748 A1 | 4/2011 | Jangra |
| 2011/0106178 A1 | 5/2011 | Schwab |
| 2011/0112533 A1 | 5/2011 | Venturini et al. |
| 2011/0112580 A1 | 5/2011 | Clement et al. |
| 2011/0137345 A1 | 6/2011 | Stoll et al. |
| 2011/0152936 A1 | 6/2011 | Gil et al. |
| 2011/0196425 A1 | 8/2011 | Rezach et al. |
| 2011/0245872 A1 | 10/2011 | Nilsson |
| 2011/0245878 A1 | 10/2011 | Franks et al. |
| 2011/0307018 A1 | 12/2011 | Zucherman et al. |

(56) References Cited

U.S. PATENT DOCUMENTS

| | | |
|---|---|---|
| 2012/0029571 A1 | 2/2012 | Schwab et al. |
| 2012/0059421 A1 | 3/2012 | Aferzon |
| 2012/0071926 A1 | 3/2012 | Jani et al. |
| 2012/0083845 A1 | 4/2012 | Winslow et al. |
| 2012/0095512 A1 | 4/2012 | Nihalani |
| 2012/0130436 A1* | 5/2012 | Haskins ............ A61B 17/7032 606/301 |
| 2012/0158064 A1 | 6/2012 | Kroll |
| 2012/0203278 A1 | 8/2012 | Gil et al. |
| 2012/0221053 A1 | 8/2012 | Copf |
| 2012/0226316 A1* | 9/2012 | Dant ................. A61B 17/7032 606/264 |
| 2012/0232593 A1 | 9/2012 | Predick |
| 2012/0232595 A1 | 9/2012 | Holschlag |
| 2012/0259369 A1* | 10/2012 | Hammer ............ A61B 17/7052 606/251 |
| 2012/0290013 A1 | 11/2012 | Simonson |
| 2012/0296335 A1 | 11/2012 | Mullaney |
| 2012/0303062 A1 | 11/2012 | Amstutz et al. |
| 2013/0018422 A1 | 1/2013 | Rinner et al. |
| 2013/0030468 A1 | 1/2013 | Le Couedic et al. |
| 2013/0079826 A1 | 3/2013 | Simonson |
| 2013/0085534 A1 | 4/2013 | Hainard et al. |
| 2013/0096617 A1 | 4/2013 | Ballard et al. |
| 2013/0123854 A1 | 5/2013 | Kondrashov et al. |
| 2013/0211457 A1 | 8/2013 | Dickinson et al. |
| 2013/0253588 A1 | 9/2013 | Traynelis et al. |
| 2013/0268004 A1 | 10/2013 | Rathbun |
| 2013/0274807 A1 | 10/2013 | Prajapati |
| 2013/0274808 A1 | 10/2013 | Larroque-Lahitette et al. |
| 2014/0018858 A1 | 1/2014 | Laeng et al. |
| 2014/0066990 A1 | 3/2014 | Akbarnia et al. |
| 2014/0088650 A1 | 3/2014 | Taddia et al. |
| 2014/0114359 A1 | 4/2014 | Hawkes |
| 2014/0135839 A1 | 5/2014 | Frankel et al. |
| 2014/0148856 A1 | 5/2014 | Ibarra et al. |
| 2014/0222076 A1 | 8/2014 | Jackson |
| 2014/0249581 A1 | 9/2014 | Stachniak |
| 2014/0277146 A1 | 9/2014 | Li et al. |
| 2014/0277160 A1 | 9/2014 | Ziolo |
| 2014/0277163 A1 | 9/2014 | Kretzer et al. |
| 2014/0303674 A1 | 10/2014 | Sasing |
| 2014/0316468 A1 | 10/2014 | Keiser et al. |
| 2014/0336706 A1 | 11/2014 | Garamszegi |
| 2014/0343613 A1 | 11/2014 | Eliasen et al. |
| 2015/0032160 A1 | 1/2015 | Carbone et al. |
| 2015/0057707 A1 | 2/2015 | Barrus et al. |
| 2015/0057708 A1 | 2/2015 | Ballard et al. |
| 2015/0073479 A1 | 3/2015 | Rinner |
| 2015/0094769 A1 | 4/2015 | Abbasi |
| 2015/0119941 A1* | 4/2015 | Daniels ............ A61B 17/7052 606/276 |
| 2015/0190178 A1 | 7/2015 | McCarthy et al. |
| 2015/0196328 A1 | 7/2015 | Hirschl et al. |
| 2015/0223844 A1 | 8/2015 | Left et al. |
| 2015/0230830 A1* | 8/2015 | Frankel ............ A61B 17/7002 606/279 |
| 2015/0282842 A1 | 10/2015 | Beyar et al. |
| 2015/0313645 A1 | 11/2015 | Hansell |
| 2015/0359568 A1 | 12/2015 | Rezach |
| 2016/0135846 A1 | 5/2016 | Mirda |
| 2016/0143665 A1 | 5/2016 | Biedermann et al. |
| 2016/0166289 A1 | 6/2016 | Alsup et al. |
| 2016/0287294 A1 | 10/2016 | Kubo et al. |
| 2017/0020578 A1 | 1/2017 | Mosnier et al. |
| 2017/0079690 A1 | 3/2017 | Oberlander et al. |
| 2017/0086885 A1 | 3/2017 | Duncan et al. |
| 2017/0086895 A1 | 3/2017 | Barra et al. |
| 2017/0095271 A1 | 4/2017 | Faulhaber |
| 2017/0105764 A1 | 4/2017 | Williams |
| 2017/0112540 A1 | 4/2017 | Montello et al. |
| 2017/0119439 A1 | 5/2017 | Ozdil et al. |
| 2017/0128105 A1 | 5/2017 | Patrinicola et al. |
| 2017/0128107 A1 | 5/2017 | Alsup et al. |
| 2017/0209182 A1 | 7/2017 | Picetti et al. |
| 2017/0245900 A1 | 8/2017 | Rezach |
| 2017/0281247 A1 | 10/2017 | Murray et al. |
| 2017/0311985 A1 | 11/2017 | Bobbitt et al. |
| 2017/0333087 A1 | 11/2017 | Lee et al. |
| 2017/0333088 A1 | 11/2017 | Lee et al. |
| 2017/0348026 A1* | 12/2017 | Stein ................. A61B 17/7032 |
| 2018/0042647 A1 | 2/2018 | Cowan et al. |
| 2018/0098798 A1 | 4/2018 | Italiaie et al. |
| 2018/0116695 A1 | 5/2018 | Armstrong et al. |
| 2018/0161073 A1 | 6/2018 | Lee et al. |
| 2018/0168694 A1 | 6/2018 | Lee et al. |
| 2018/0195150 A1 | 7/2018 | Meyer et al. |
| 2018/0206890 A1 | 7/2018 | Rezach |
| 2018/0228516 A1* | 8/2018 | Armstrong ........ A61B 17/7035 |
| 2018/0228518 A1 | 8/2018 | Carruth et al. |
| 2018/0243009 A1 | 8/2018 | Bobbitt et al. |
| 2018/0280062 A1 | 10/2018 | Lee et al. |
| 2018/0280063 A1 | 10/2018 | Lee et al. |
| 2018/0317972 A1 | 11/2018 | Abbasi |
| 2019/0167313 A1 | 6/2019 | Ortiz et al. |
| 2019/0175226 A1 | 6/2019 | Carruth et al. |
| 2019/0183541 A1 | 6/2019 | Lee et al. |
| 2019/0269440 A1 | 9/2019 | Patrinicola et al. |
| 2019/0336178 A1 | 11/2019 | Finn et al. |
| 2019/0365432 A1 | 12/2019 | Lee et al. |
| 2020/0060729 A1 | 2/2020 | Lee et al. |
| 2020/0069341 A1 | 3/2020 | Abbasi |
| 2020/0085473 A1 | 3/2020 | Lee et al. |
| 2020/0170695 A1 | 6/2020 | Lee et al. |
| 2021/0186572 A1 | 6/2021 | Lee et al. |
| 2022/0039835 A1 | 2/2022 | Lee et al. |
| 2022/0323130 A1 | 10/2022 | Lee et al. |

FOREIGN PATENT DOCUMENTS

| | | |
|---|---|---|
| EP | 1857064 A1 | 11/2007 |
| EP | 2 319 436 A1 | 5/2011 |
| EP | 2730242 A1 | 5/2014 |
| JP | H09-503148 A | 3/1997 |
| JP | 2001517122 A | 10/2001 |
| JP | 2003515380 A | 5/2003 |
| JP | 2003526442 A | 9/2003 |
| JP | 2007530223 A | 11/2007 |
| JP | 2008523890 A | 7/2008 |
| JP | 2009522021 A | 6/2009 |
| JP | 2009533087 A | 9/2009 |
| JP | 2010506670 A | 3/2010 |
| JP | 2010540112 A | 12/2010 |
| JP | 2014097405 A | 5/2014 |
| JP | 2014521383 A | 8/2014 |
| JP | 2016501690 A | 1/2016 |
| KR | 20100054713 A | 5/2010 |
| WO | 2005/044119 A2 | 5/2005 |
| WO | 2007124242 A1 | 11/2007 |
| WO | 2009076107 A1 | 6/2009 |
| WO | 2009/110865 A8 | 12/2009 |
| WO | 2011/004222 A1 | 1/2011 |
| WO | 2011/006155 A1 | 1/2011 |
| WO | 2015/017250 A1 | 2/2015 |

OTHER PUBLICATIONS

U.S. Appl. No. 15/377 449, filed Dec. 13 2016, Implant Adaptors and Related Methods.

U.S. Appl. No. 15/382,837, filed Dec. 19, 2016, Offset Rods, Offset Rod Connectors, and Related Methods.

U.S. Appl. No. 15/284 587, filed Oct. 4 2016, Implant Connectors and Related Methods.

U.S. Appl. No. 15/430,188, filed Feb. 10, 2017, Tandem Rod Connectors and Related Methods.

U.S. Appl. No. 15/471,075, filed Mar. 28 2017, Articulating Implant Connectors and Related Methods.

U.S. Appl. No. 15/828,805, filed Dec. 1, 2017, Rod-to-Rod Connectors Having Robust Rod Closure Mechanisms and Related Methods.

U.S. Appl. No. 15/843,618, filed Dec. 15 2017, Unilateral Implant Holders and Related Methods.

(56) References Cited

OTHER PUBLICATIONS

U.S. Appl. No. 15/926,051, filed Mar. 20, 2018, Articulating Implant Connectors and Related Methods.
U.S. Appl. No. 16/280,918, filed Feb. 20, 2019, Tandem Rod Connectors and Related Methods.
U.S. Appl. No. 16/443,849, filed Jun. 17 2019, Implant Connectors and Related Methods.
U.S. Appl. No. 16/666,887, filed Oct. 29, 2019, Offset, Rods, Offset Rod Connectors, and Related Methods.
U.S. Appl. No. 16/688,578, filed Nov. 19, 2019, Implant Connectors and Related Methods.
U.S. Appl. No. 16/782,030, filed Feb. 4 2020, Articulating Implant Connectors and Related Methods.
Chinese Office Action for Application No. 201780030641.3, dated Nov. 1, 2021 (15 pages).
Japanese Office Action for Application No. 2019-543334, dated Nov. 9, 2021 (16 pages).
Japanese Office Action for Application No. 2019-553450, dated Dec. 14, 2021 (19 pages).
[No Author Listed] VuePoint II Technique Guide, 2015, NuVasive®, Inc.; 64 pages.
Akbarnia, B., et al., "Pediatric Isola® Prebent Rod Placement," (Technique Manual), DePuy Acromed, Oct. 2010; 2 pages.
International Search Report and Written Opinion for Application No. PCT/US2017/031883, dated Aug. 2, 2017. (15 pgs).
International Search Report and Written Opinion for Application No. PCT/US2018/017034, dated Aug. 1, 2018 (20 pages).
Invitation to Pay Additional Fees for Application No. PCT/US2018/017034, dated May 18, 2018 (18 pages).
International Search Report and Written Opinion for Application No. PCT/US2018/024731, dated Jul. 2, 2018 (17 pages).
International Search Report and Written Opinion for Application No. PCT/US2018/062786, dated Feb. 4, 2019 (5 pages).
Chinese Search Report for Application No. 201880023022.6, dated Jul. 7, 2022 (3 pages).
Japanese Office Action for Application No. 2018-560664, dated Apr. 21, 2021 (6 pages) Translation Only.

* cited by examiner

TANDEM ROD CONNECTORS AND RELATED METHODS

CROSS-REFERENCE TO RELATED APPLICATIONS

This application is a continuation of U.S. application Ser. No. 16/280,918, filed Feb. 20, 2019. U.S. application Ser. No. 16/280,918 is a continuation of U.S. application Ser. No. 15/430,188, filed on Feb. 10, 2017 (now issued as U.S. Pat. No. 10,238,432). The entire contents of each of these applications are incorporated by reference herein.

FIELD

Orthopedic devices and methods are disclosed herein, including tandem rod connectors and related methods.

BACKGROUND

Fixation systems can be used in orthopedic surgery to align and/or fix a desired relationship between two or more bones or bone fragments. For example, in spinal surgery, spinal fixation systems can be used to align and/or fix a desired relationship between vertebrae. A typical spinal fixation system can include bone screws or other anchors implanted in the vertebrae and connected by longitudinal rods.

There are a number of instances in which it can be desirable or necessary to arrange multiple rods in tandem. For example, rods might be arranged in tandem when adding a rod to an existing construct to extend the construct to additional vertebral levels, or when seeking to achieve a rod offset to clear other implants or patient anatomy, or to better fit with a series of implanted bone anchors. There are also a number of instances in which it can be desirable or necessary to attach multiple rods to the same bone anchor. This can arise, for example, when insufficient space or poor bone quality prevents use of a separate bone anchor at a particular location, or prevents use of a connector that attaches directly to both rods. Existing solutions for attaching multiple rods may be bulky, may require a large offset between the rods, or may limit the flexibility with which one rod can be positioned relative to another.

Accordingly, there is a need for improved rod connectors and related methods.

SUMMARY

Connectors are disclosed herein that can be used to attach a rod to a bone anchor assembly that is already occupied by a separate rod. Various ways of attaching the connector to the bone anchor assembly are disclosed, including arrangements in which the connector is locked to the bone anchor, arrangements in which the connector is constrained in one or more degrees of freedom relative to the bone anchor, arrangements in which the connector is adjustable in one or more degrees of freedom relative to the bone anchor, and arrangements that include a spherical articulation joint. In some embodiments, attachment of the connector to a bone anchor can be aided with the use of a positioner. The geometry of the connector can be selected to minimize the offset between a first rod received in the bone anchor assembly and a second rod received in the connector, for example using an angled or curved rod recess and/or a fastener, or set screw, that is offset from the center of the rod or angled relative to the bone anchor. The connector can be configured to align the first and second rods in a common coronal plane, or can be configured to position one rod more anterior or posterior than the other rod.

In some embodiments, a connector assembly can include a connector having a proximal end and a distal end that define a proximal-distal axis, the connector including: a first portion configured to mate the connector to a receiver member of a bone anchor assembly, the bone anchor assembly having a first rod-receiving recess for receiving a first rod, and a second portion in which a second rod-receiving recess is formed, the second rod-receiving recess being configured to receive a second rod; a first fastener having a distal portion configured to engage the receiver member to lock the first rod to the receiver member and a proximal portion that extends through an opening formed in the first portion of the connector; a nut mateable to the first fastener to secure the connector to the receiver member; and a second fastener engaged with the second portion of the connector to lock the second rod to the connector; wherein the second rod-receiving recess includes a proximal opening and a distal seat and wherein the proximal opening is offset from the distal seat in a direction perpendicular to the proximal-distal axis.

The first and second rods can have a rod diameter, the first and second rods can have a center-to-center offset, when seated in the receiver member and the connector, respectively, and a ratio of the center-to-center offset to rod diameter can be in the range of about 2:1 to about 4:1. The ratio of the center-to-center offset to rod diameter can be about 2:1. The first and second rods can have a center-to-center offset, when seated in the receiver member and the connector, respectively, in the range of about 6 mm to about 16 mm, e.g., in the range of about 6 mm to about 10 mm. The first and second rods can have a center-to-center offset, when seated in the receiver member and the connector, respectively, of about 8 mm. The first rod-receiving recess can include a first rod seat and the first rod seat can be distal to the seat of the second rod-receiving recess. The first rod-receiving recess can include a first rod seat and the first rod seat can be proximal to the seat of the second rod-receiving recess. The first rod-receiving recess can include a first rod seat and the first rod seat can be at substantially the same proximal-distal height as the seat of the second rod-receiving recess.

The first portion of the connector can include a recess configured to receive a proximal end of the receiver member, the recess being cylindrical such that, when the receiver member is received in the recess, the receiver member is free to rotate relative to the connector about a central axis of the receiver member. The first portion of the connector can include a recess configured to receive a proximal end of the receiver member, the recess including one or more flats that abut corresponding flats of the receiver member such that, when the receiver member is received in the recess, the receiver member is constrained to uniplanar motion relative to the connector. The first portion of the connector can include a recess configured to receive a proximal end of the receiver member, the recess forming a substantial negative of the receiver member such that, when the receiver member is received in the recess, the receiver member cannot rotate or translate relative to the connector. The first portion of the connector can include a domed distal-facing surface that bears against a proximal-facing surface of the receiver member in a gimbal interface. The opening in the first portion of the connector can be oversized relative to the first fastener to allow movement of the connector relative to the receiver member. The assembly can include a positioner having a central opening in which the first fastener is received and distally-extending tabs that engage the receiver member to limit rotation between the positioner and the receiver member.

The positioner can include teeth configured to be selectively enmeshed with teeth of the connector to limit rotation between the connector and the receiver member. The positioner can include a flat formed on an outer sidewall of the positioner and configured to selectively engage a flat formed on an inner sidewall of the connector to limit rotation between the connector and the receiver member. Tightening the nut can be effective to clamp the tabs of the positioner onto the first fastener. The nut can have a spherical exterior surface received within a spherical interior surface of the opening formed in the first portion of the connector to allow the connector to move polyaxially relative to the receiver member. The nut can include a conical distal-facing surface that contacts a conical proximal-facing surface of the connector. The conical surfaces of the nut and the connector can taper at angles that differ from one another. The conical surfaces of the nut and the connector can taper at the same angle. The nut can be a locking nut configured to expand within the opening to lock an orientation of the connector relative to the receiver member.

At least one of the first fastener and a throughbore of the locking nut can have a tapered thread such that rotation of the locking nut relative to the first fastener is effective to radially expand the locking nut. The locking nut can have a castle drive feature with curved abutment surfaces. A distal surface of the connector can be configured to constrain movement of the connector relative to the receiver member to a direction parallel to the first rod. A distal surface of the connector can be configured to constrain movement of the connector relative to the receiver member to a direction perpendicular to the first rod. The second rod can be positionable in the second rod-receiving recess by moving the second rod distally relative to the connector. The second rod-receiving recess can follow a curved path between the proximal opening and the distal seat.

The second rod-receiving recess can follow a path that is obliquely angled relative to the proximal-distal axis of the connector. In some embodiments, a rotation axis of the second fastener does not intersect with a central longitudinal axis of the second rod when the second rod is seated in the connector. A rotation axis of the second fastener can extend at an oblique angle with respect to the proximal-distal axis of the connector. The second fastener can be a set screw and the set screw can be received within a set screw recess formed in the connector, the center of the set screw recess can be offset in a direction perpendicular to the proximal-distal axis from a center of the proximal opening of the second rod-receiving recess. The distal seat of the second rod-receiving recess can define a V-shape configured to receive rods of different diameters. The assembly can include the bone anchor assembly, the first rod, and the second rod.

In some embodiments, a connector assembly can include a connector that includes an opening that defines a spherical interior surface and a rod-receiving recess laterally offset from the opening and configured to receive an elongate spinal rod; a threaded fastener; and a locking nut received within the opening of the connector, the locking nut having a spherical exterior surface and a threaded throughbore in which a proximal end of the fastener is received; wherein the assembly has an unlocked configuration in which the connector is polyaxially movable relative to the fastener and a locked configuration in which an orientation of the connector relative to the fastener is fixed, the locking nut being radially expanded in the locked configuration as compared to the unlocked configuration.

The threads of the fastener or the threads of the locking nut can be tapered such that rotation of the locking nut relative to the fastener is effective to radially expand the locking nut. The locking nut can have a castle drive feature with curved abutment surfaces. A distal surface of the connector can include a first planar portion and a second planar portion oriented at an oblique angle with respect to the first planar portion to constrain movement of the connector relative to a receiver member in which the set screw is disposed.

In some embodiments, a spinal fixation method can include implanting a bone anchor assembly in a vertebra of a patient, the bone anchor assembly including a receiver member having a first rod-receiving recess; inserting a first rod into the first rod-receiving recess of the receiver member; inserting a first fastener into the receiver member to secure the first rod in the receiver member; positioning a connector over the receiver member such that a proximal portion of the first fastener extends through an opening formed in the connector; inserting a second rod into a second rod-receiving recess formed in the connector; inserting a second fastener into a fastener recess formed in the connector to secure the second rod in the connector; adjusting an orientation of the connector relative to the receiver member to achieve a desired positioning of the first and second rods; and tightening a nut on the first fastener to fix the orientation of the connector relative to the receiver member.

The method can include positioning the first and second rods such that a center-to-center offset between the first and second rods is in the range of about 6 mm to about 16 mm, e.g., in the range of about 6 mm to about 10 mm. The method can include positioning the first and second rods such that a ratio of a center-to-center offset, between the first and second rods, to a diameter of the first and second rods is in the range of about 2:1 to about 4:1. The method can include positioning the first and second rods such that a ratio of a center-to-center offset, between the first and second rods, to a diameter of the first and second rods is about 2:1. The method can include placing a positioner between the connector and the receiver member, wherein the positioner restricts relative rotation between the connector and the receiver member about the first fastener after the nut is tightened. The method can include positioning the first and second rods such that the first rod is anterior to the second rod. The method can include positioning the first and second rods such that the first and second rods substantially lie in a common coronal plane. Inserting the second rod can include moving the rod distally and laterally within a curved rod-receiving recess. Inserting the second rod can include moving the rod distally and laterally within an obliquely angled rod-receiving recess. Inserting the second rod can include top loading the rod into the connector. Adjusting the orientation can include pivoting the connector about at least one of a uniplanar interface, a gimbal interface, and a spherical articulation joint.

BRIEF DESCRIPTION OF THE DRAWINGS

The following detailed description is provided with the accompanying drawings, in which.

DETAILED DESCRIPTION

Connectors are disclosed herein that can be used to attach a rod to a bone anchor assembly that is already occupied by a separate rod. Various ways of attaching the connector to the bone anchor assembly are disclosed, including arrangements in which the connector is locked to the bone anchor, arrangements in which the connector is constrained in one or more degrees of freedom relative to the bone anchor, arrangements in which the connector is adjustable in one or more degrees of freedom relative to the bone anchor, and arrangements that include a spherical articulation joint. In some embodiments, attachment of the connector to a bone anchor can be aided with the use of a positioner. The geometry of the connector can be selected to minimize the offset between a first rod received in the bone anchor assembly and a second rod received in the connector, for example using an angled or curved rod recess and/or a fastener, or set screw, that is offset from the center of the rod or angled relative to the bone anchor. The connector can be configured to align the first and second rods in a common coronal plane, or can be configured to position one rod more anterior or posterior than the other rod.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

Figure 1A:
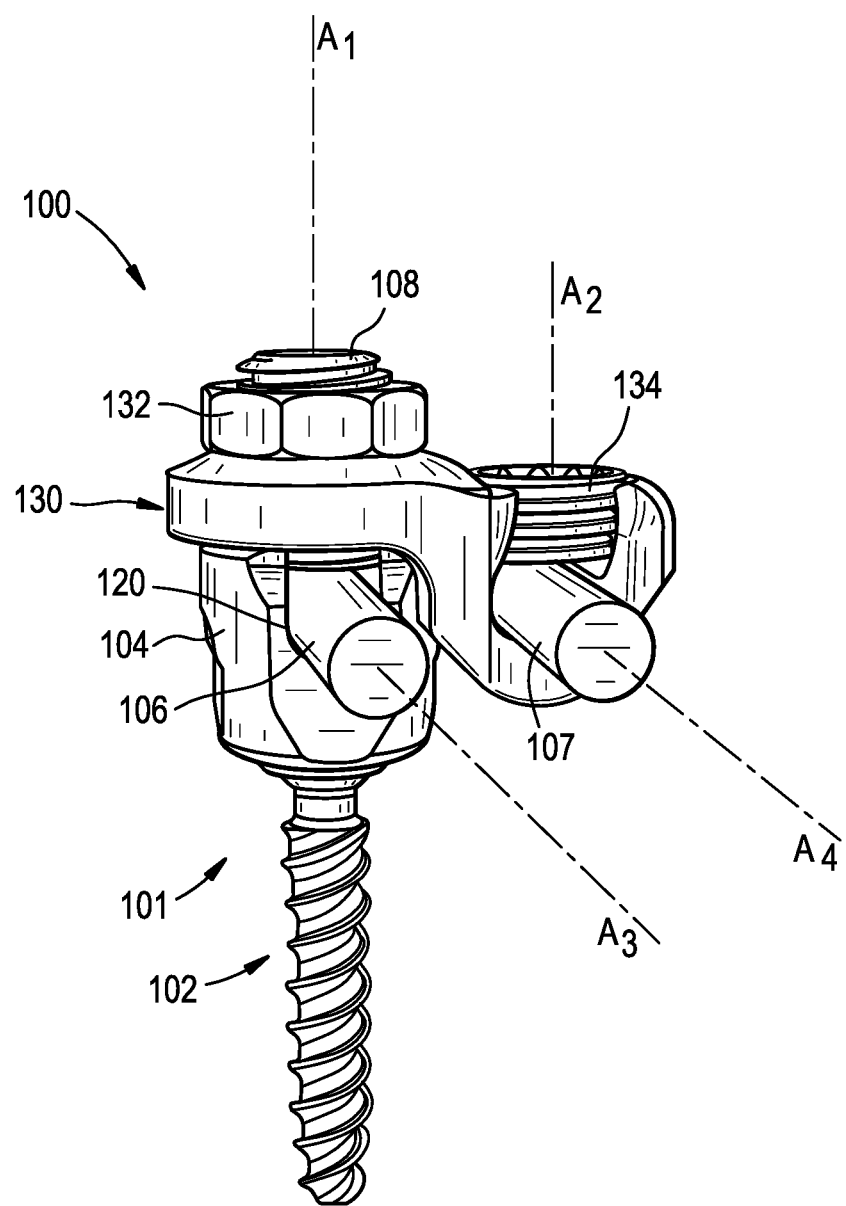
FIG. 1A is a perspective view of a connector assembly shown with a bone anchor and first and second rods.
Figure 1B:
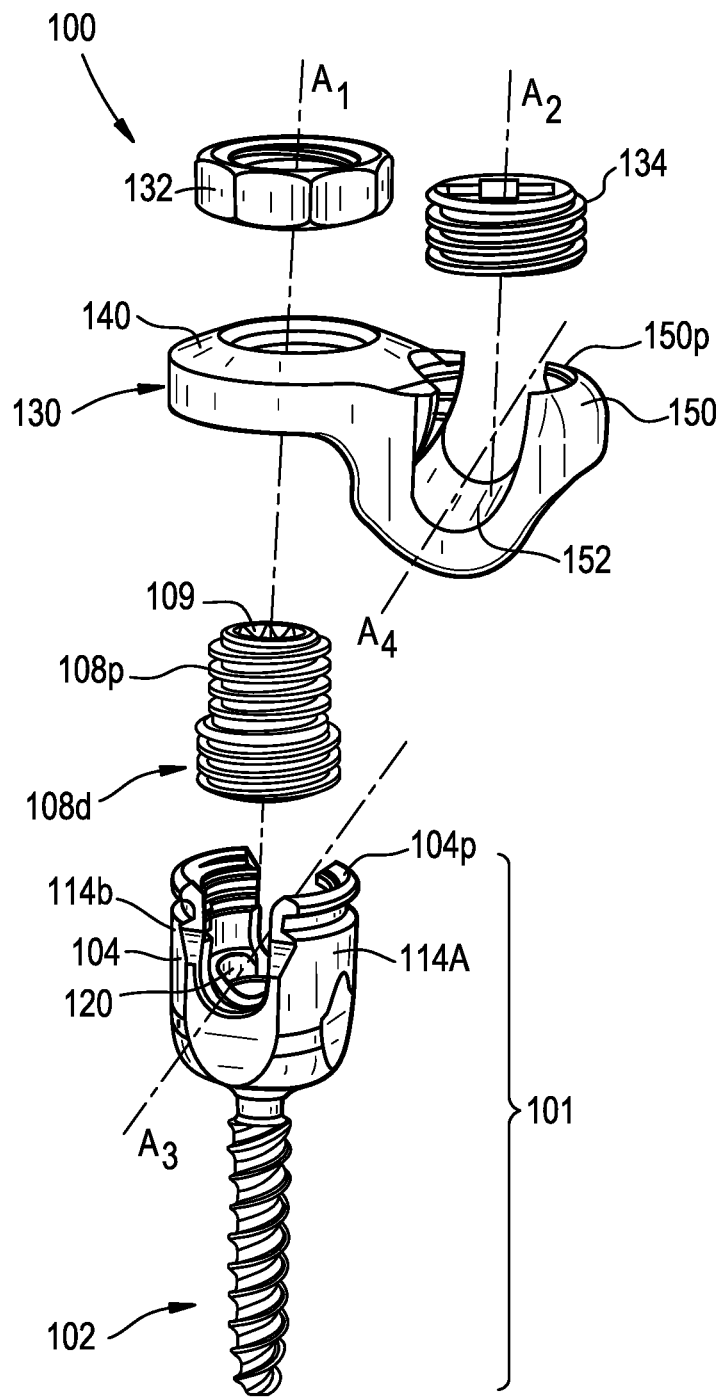
FIG. 1B is an exploded perspective view of the connector assembly and bone anchor of FIG. 1A.

FIGS. 1A-1E illustrate an exemplary embodiment of a connector assembly 100 which can be used, for example, to connect a second spinal rod 107 to a bone anchor assembly 101 in which a first spinal rod 106 is received. The connector assembly 100 can include a connector 130 having a first portion 140 for mating the connector with a bone anchor assembly 101 and a second portion 150 for mating the connector with a fixation element such as the illustrated rod 107. As described further below, the first portion 140 of the connector 130 can receive, fit over, or otherwise interact with a proximal portion 104p of a head or receiver member 104 of the bone anchor assembly 101. The connector 130 can be attached to the receiver member 104 in various ways, for example using a first fastener, or set screw, 108 and a nut 132 as shown in FIGS. 1A-1B. The set screw 108 can include a distal portion 108d received in the receiver member 104 and a proximal portion 108p that extends through an opening 142 in the connector 130 and on which the nut 132 can be threaded. The nut 132 can be tightened to lock the connector 130 relative to the receiver member 104. The second portion 150 of the connector 130 can be disposed adjacent to the first portion 140. The second portion 150 can include a rod-receiving recess or channel 152 sized and configured to receive a spinal rod 107 therein. A second fastener, set screw or other closure mechanism, 134 can be secured within a proximal opening 156 of the second portion 150 of the connector 130 to lock a spinal rod 107 therein. While first and second set screws are shown, other fasteners can be used instead or in addition, such as quarter-turn closure caps, nuts, etc.

An exemplary bone anchor assembly 101 is shown in FIGS. 1A-1B and described below, though it will be appreciated that the connector assembly 100 can be used with any of a variety of bone anchor assemblies. Other exemplary bone anchor assemblies and associated features are disclosed in U.S. Pat. No. 6,736,820 issued May 18, 2004, U.S. Pat. No. 6,974,460 issued Dec. 13, 2005, U.S. Pat. No. 7,179,261 issued Feb. 20, 2007, U.S. Pat. No. 9,155,580 issued Oct. 13, 2015, U.S. Pat. No. 9,265,548 issued Feb. 23, 2016, and U.S. Pat. No. 9,433,445 issued Sep. 6, 2016, each of which is hereby incorporated by reference in its entirety. The illustrated bone anchor assembly 101 generally includes a proximal head or receiver member 104 and a threaded distal shank or bone anchor 102. The bone anchor 102 can be formed integrally with the receiver member 104 or can be a separate component movably coupled to the receiver member. In the latter configuration, the bone anchor 102 can be selectively locked in any of a variety of orientations relative to the receiver member 104. For example, prior to locking, the bone anchor 102 can be polyaxially movable relative to the receiver member 104 within a cone of angulation generally defined by the geometry of the distal end of the receiver member and the proximal head of the bone anchor. The bone anchor assembly 101 can be locked to maintain the bone anchor 102 at fixed orientation relative to the receiver member 104. The bone anchor assembly 101 can be a favored angle screw, a conventional (non-biased) polyaxial screw, a monoaxial screw, a uniplanar screw, a hook, or any of a variety of other bone anchor types known in the art.

The first fixation element or rod 106 can be received within the receiver member 104. The first rod 106 can directly contact the proximal head of the bone anchor 102 or can contact an intermediate element such as a compression cap or collet (not shown). For example, a compression member can be positioned within the receiver member 104 and interposed between the spinal rod 106 and the proximal head of the bone anchor 102 to compress the distal outer surface of the proximal head into direct, fixed engagement with the distal inner surface of the receiver member 104. The receiver member 104 can include a central longitudinal or proximal-distal axis A1. The receiver member 104 can include a pair of spaced apart arms 114A, 114B that define a first rod-receiving recess or channel 120 for receiving the spinal rod 106. The channel 120 can be U-shaped as shown or can have various other configurations. A rod 106 seated in the channel 120 can have a central longitudinal axis A3 that is perpendicular to the axis A1 of the receiver member 104.

In the illustrated embodiment, the first rod 106 is an elongate cylindrical spinal rod, though it will be appreciated that the first rod can take other forms, such as bone plates, wires, tethers, and the like. While the illustrated first rod 106 has a circular cross-section, any of a variety of cross-sections can be used such as oval, oblong, square, rectangular, triangular, hexagonal, and so forth. The first rod 106 can have any of a variety of diameters. In some embodiments, the diameter can be in the range of about 2.5 mm to about 7.5 mm. For example, the diameter can be about 2.5 mm, about 3.0 mm, about 3.5 mm, about 4.0 mm, about 4.5 mm, about 5.0 mm, about 5.5 mm, about 6.0 mm, about 6.5 mm, about 7.0 mm, or about 7.5 mm. The first rod 106 can be substantially straight along its length, or can include one or more bends or curves formed therein. The first rod 106 can be malleable or bendable such that it can be bent before or during a procedure to achieve a desired correction.

The proximal end of the channel 120 formed in the receiver member 104 can be configured to receive a closure mechanism 108 positionable between and engaging the arms 114A, 114B of the receiver member. The closure mechanism 108 can be selectively secured to the receiver member 104 to capture a spinal fixation element, e.g., the first rod 106, within the receiver member. Tightening or locking the closure mechanism 108 can be effective to fix the first rod 106 relative to the receiver member 104, and to fix an angular position of the bone anchor 102 relative to the receiver member 104. The illustrated closure mechanism 108 is in the form of a threaded post with an enlarged-diameter distal portion 108$d$ and a reduced-diameter proximal portion 108$p$. In other embodiments, the proximal and distal portions 108$p$, 108$d$ can have the same diameter, or the proximal portion can have a diameter greater than that of the distal portion. The distal portion 108$d$ of the closure mechanism 108 can be threaded into the receiver member 104 to engage the first rod 106 disposed in the receiver member 104. The proximal portion 108$p$ of the closure mechanism 108 can protrude above the receiver member 104, e.g., above a proximal-facing terminal end surface of the receiver member, and through an opening 142 formed in the connector 130, as described further below.

In the illustrated embodiment, the closure mechanism 108 bears directly against the spinal rod 106, which in turn bears directly against the head of the bone anchor 102. It will be appreciated, however, that one or more intermediate elements can also be included in the bone anchor assembly 101. For example, the bone anchor assembly 101 can include a compression member disposed between the spinal rod 106 and the head of the bone anchor 102. The closure mechanism 108 can be a single set screw as shown, or can include an outer set screw operable to act on a compression member and an inner set screw operable to act on the rod 106. Use of an inner and outer set screw can allow for independent locking of (i) the bone anchor 102 orientation relative to the receiver member 104 and (ii) the rod 106 relative to the receiver member 104. The closure mechanism 108 can include a driving interface 109 (e.g., Torx, flathead, Phillips head, square, or otherwise) to facilitate rotational advancement or retraction of the closure mechanism relative to the receiver member 104 using a driver instrument.

Figure 1C:
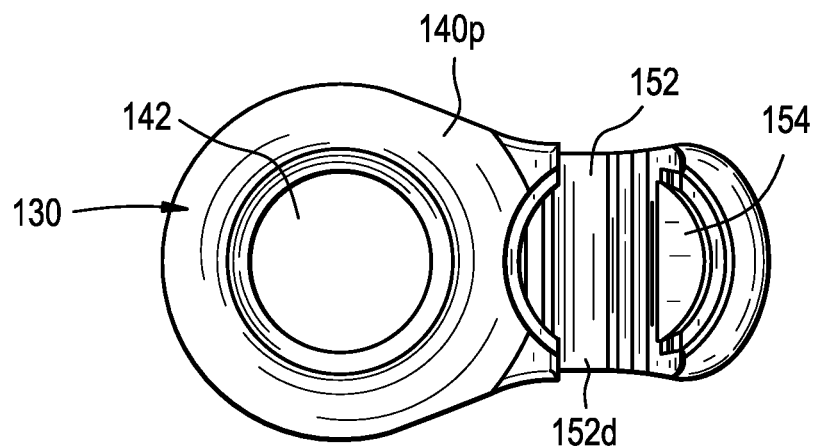
FIG. 1C is a top view of a connector of the connector assembly of FIG. 1A.
Figure 1D:
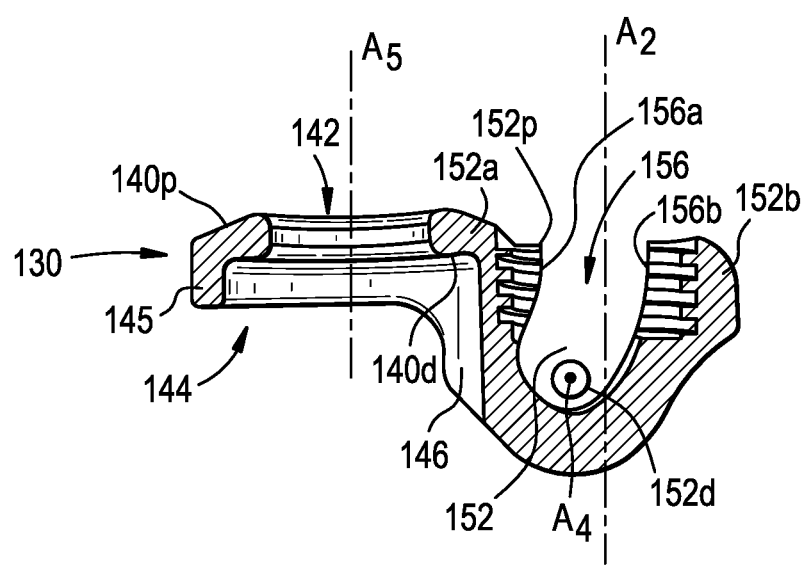
FIG. 1D is a sectional side view of the connector of FIG. 1C.
Figure 1E:
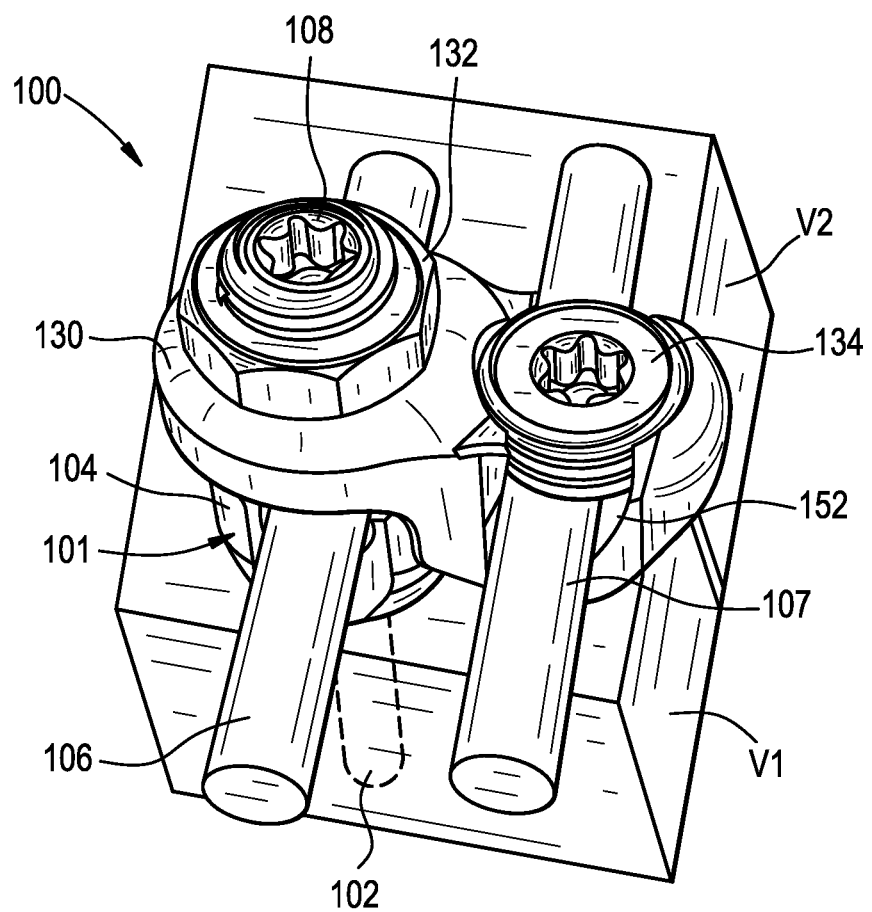
FIG. 1E is a perspective view of the connector assembly, bone anchor, and rods of FIG. 1A secured to a patient's vertebra.

As noted above, the connector 130 can include a first portion 140 and a second portion 150. The first portion 140 can have a proximal-facing surface 140$p$ and a distal-facing surface 140$d$. As shown in FIG. 1C, the first portion 140 can include a through hole 142 extending from the proximal-facing surface 140$p$ to the distal-facing surface 140$d$. The through hole 142 can be sized to receive the proximal portion 108$p$ of the set screw 108 therethrough. As shown in FIG. 1D, the through-hole 142 can have a central longitudinal axis A5. The axis A5 can be collinear or substantially collinear with the longitudinal axis A1 when the connector 130 is installed on the receiver member 104, or can be offset or obliquely angled with respect to the axis A1. The set screw 108 can be inserted through the through-hole 142 of the connector 130 to allow the connector to sit on the receiver member 104, e.g., on a proximal-facing end surface of the receiver member.

The first portion 140 of the connector 130 can include various geometries or features for interacting with the receiver member 104. For example, as shown in FIG. 1D, the first portion 140 can define a recess 144 sized to receive at least a portion of the receiver member 104 therein. The recess 144 can be defined by an annular or substantially annular sidewall 145 that extends distally from the distal-facing surface 140d. As described further below with respect to FIGS. 4A-5C, the geometry of the recess 144 can be selected to constrain movement of the connector 130 in one or more degrees of freedom with respect to the receiver member 104, or to allow for adjustment of the connector 130 in one or more degrees of freedom with respect to the receiver member 104. In the embodiment shown in FIG. 1D, the inner surface 146 of the sidewall 145 is cylindrical or substantially cylindrical, which can allow the connector 130 to rotate about the axis A5 relative to the receiver member 104 when the receiver member is disposed in the recess 144, e.g., when a proximal-facing end surface of the receiver member is seated against the distal facing surface 140d of the connector.

The sidewall 145 can form a negative of at least a portion of the receiver member 104. For example, the inner surface 146 can form a negative of a curved outer sidewall portion of the receiver member 104, such that the connector 130 can hug the receiver member 104 with minimal or zero gap therebetween. The inner surface 146 can be concave with a radius of curvature equal or substantially equal to a radius of curvature of the exterior sidewall of the receiver member 104.

With the proximal portion 108p of the set screw 108 inserted through the opening 142 in the connector 130, the nut 132 can be threaded onto the set screw 108 to secure the connector 130 to the receiver member 104. When tightened, the nut 132 can lock the position and orientation of the connector 130 relative to the receiver member 104. The position of the connector 130 can be adjusted prior to tightening the nut 132 to achieve the desired orientation of the second rod 107 relative to the first rod 106. The nut 132 can include a distal-facing surface configured to cooperate with the proximal-facing surface 140p of the connector 130. For example, the proximal-facing surface 140p of the connector 130 can have a domed or spherical shape and the distal-facing surface of the nut 132 can have a corresponding domed or spherical shape. This arrangement can facilitate locking of the connector 130 to the receiver member 104 when the connector is angled or pivoted relative to the receiver member, as described further below. The nut 132 and the proximal-facing surface 140p of the connector can cooperate in the manner described further below with respect to the corresponding components of FIGS. 7A-7L.

The second portion 150 of the connector 130 can define a second rod-receiving recess or channel 152 for receiving the second rod 107 therein. The assembly 100 can be configured such that, when first and second rods 106, 107 are received therein, the longitudinal axes A3, A4 of the rods 106, 107 are offset from one another in one or more planes, e.g., in a coronal plane, in a sagittal plane, or in both coronal and sagittal planes of the patient. It will be appreciated that the diameter of the first rod 106 can be less than, equal to, or greater than the diameter of the second rod 107. As shown, the second rod 107 is an elongate cylindrical spinal rod, though it will be appreciated that, like the first rod 106, the second rod 107 can take other forms, such as bone plates, wires, tethers, and the like. It will also be appreciated that, while the illustrated second rod 107 has a circular cross-section, any of a variety of cross-sections can be used such as oval, oblong, square, rectangular, triangular, hexagonal, and so forth. The second rod 107 can have any of a variety of diameters. In some embodiments, the diameter of the second rod 107 can be in the range of about 2.5 mm to about 7.5 mm. For example, the diameter of the second rod 107 can be about 2.5 mm, about 3.0 mm, about 3.5 mm, about 4.0 mm, about 4.5 mm, about 5.0 mm, about 5.5 mm, about 6.0 mm, about 6.5 mm, about 7.0 mm, or about 7.5 mm. The second rod 107 can be substantially straight along its length, or can include one or more bends or curves formed therein. The second rod 107 can be malleable or bendable such that it can be bent before or during a procedure to achieve a desired correction. A rod 107 seated in the channel 152 can have a central longitudinal axis A4.

The second rod-receiving recess 152 can be defined by opposed first and second arms 152a, 152b. As shown, the first portion 140 of the connector 130 can be a cantilevered lateral extension of the first arm 152a. The second rod-receiving recess 152 can be open in a proximal direction, such that a rod 107 can be inserted into the recess by moving the rod distally with respect to the connector 130. Each of the arms 152a, 152b can include a feature (not shown), such as a recess, dimple, notch, projection, or the like, to facilitate coupling of the connector 130 to various instruments. For example, the outer surface of each arm 152a, 152b can include an arcuate groove at the respective proximal end of the arm for attaching the connector 130 to an extension tower or retractor. The arms 152a, 152b can include or can be coupled to extension or reduction tabs (not shown) that extend proximally from the connector 130 to functionally extend the length of the arms 152a, 152b. The extension tabs can facilitate insertion and reduction of a rod or other implant, as well as insertion and locking of the second set screw 134. The extension tabs can be configured to break away or otherwise be separated from the arms 152a, 152b. The inner surfaces of each of the arms 152a, 152b can be configured to mate with the second set screw 134. For example, the inner surfaces of the arms 152a, 152b can include threads that correspond to external threads formed on the second set screw 134. Accordingly, rotation of the second set screw 134 with respect to the connector 130 about a set screw axis A2 can be effective to translate the set screw with respect to the connector axially along the axis A2.

The proximal opening 152p of the second rod-receiving recess 152 can be formed in a proximal-facing surface 150p of the second portion 150 of the connector. The second rod 107 can be inserted through the proximal-most opening 152p of the recess 152 and advanced distally and laterally toward the distal-most seat 152d of the recess 152. Forming the second rod-receiving recess 152 such that it is open in a proximal direction as shown can advantageously allow the rod 107 to be top loaded into the connector 130, as would typically be the case with other bone anchor assemblies of the larger construct in which the rod 107 will be inserted. By matching orientations, insertion and reduction of the rod 107 can be facilitated.

The second-rod receiving recess 152 can be curved or angled. For example, the recess 152 can be a curved U-shaped channel as shown. The recess 152 can be curved or angled in a plane defined by the axes A5 and A2. Accordingly, a proximal-most opening 152p of the recess 152 can be laterally offset in a direction perpendicular to the axis A2 and perpendicular to the axis A4 relative to the distal-most seat 152d of the recess. The degree of this offset can be selected to achieve the desired center-to-center offset of the first and second rods 106, 107. In some embodiments, the connector 130 can be configured such that the first and second rods 106, 107 have a center-to-center offset in the range of about 6.0 mm to about 10.0 mm. In some embodiments, the connector 130 can be configured such that the first and second rods 106, 107 have a center-to-center offset of about 8.0 mm. A ratio of the center-to-center offset to the diameter of the first and second rods 106, 107 can be in the range of about 1:1 to about 4:1. In some embodiments, the ratio of the center-to-center offset to the diameter of the first and second rods 106, 107 can be about 2:1. Reducing the center-to-center offset of the first and second rods 106, 107 can be advantageous. For example, a small offset can facilitate use of the connector at or near the transition from cervical vertebrae to thoracic vertebrae. In this region, the trajectory of the bone anchors typically switches from medial-lateral for the cervical vertebrae to lateral-medial for the thoracic vertebrae, resulting in bone anchor heads being laterally offset from each other but still being very close. A small offset connector can allow rods disposed in these bone anchors to be coupled to one another without taking up a lot of space or without skipping a vertebral level when attaching bone anchors to the spine.

The offset between the proximal end 152$p$ and the distal end 152$d$ of the recess 152 can be achieved by curving the recess. The path of the curved recess 152 can extend along a radius of curvature, about an axis that is parallel to the axis A4. In some embodiments, the radius of curvature can be in the range of about 5.0 mm to about 10.0 mm. In some embodiments, the radius of curvature can be about 7.5 mm.

The offset between the proximal end 152$p$ and the distal end 152$d$ of the recess 152 can alternatively be achieved by angling the recess. For example, the walls of the recess 152 can extend at an oblique angle with respect to the axis A5 of the connector 130. In some embodiments, the walls of the recess 152 can extend at an angle in the range of about 10 degrees to about 20 degrees relative to the axis A5. In some embodiments, the walls of the recess 152 can extend at an angle of about 15 degrees relative to the axis A5.

In the illustrated embodiment, the central axis A3 of the first rod 106 and the central axis A4 of the second rod 107 lie in the same coronal plane when the assembly 100 is implanted in a patient, such that the first and second rods 106, 107 overlap in the sagittal view. In other embodiments, for example as discussed below with respect to FIGS. 8-9C, the rods 106, 107 can be non-overlapping in the sagittal view. For example, the second rod 107 can be disposed anterior to the first rod 106 or posterior to the first rod 106.

In the illustrated embodiment, the central axis A3 of the first rod 106 and the central axis A4 of the second rod 107 are parallel to one another. In other embodiments, the connector 130 can be configured such that the central axis A3 of the first rod 106 is perpendicular or obliquely angled with respect to the central axis A4 of the second rod 107.

As shown in FIGS. 1C and 1D, the connector 130 can include a threaded recess 156 defined by the first and second arms 152$a$, 152$b$ for receiving the second set screw 134. The set screw recess 156 can be generally circular and can have a center that is laterally offset from the center of the proximal opening 152$p$ of the second rod-receiving recess 152. The set screw recess 156 can include threads 156$a$ formed on the first arm 152$a$ and threads 156$b$ formed on the second arm 152$b$. In the illustrated embodiment, the set screw 134 bears directly against the second rod 107, which in turn bears directly against the rod seat 152$d$ in the distal end of the second rod-receiving channel 152. It will be appreciated, however, that one or more intermediate elements can also be included. The set screw 134 can include a driving interface (e.g., Torx, flathead, Phillips head, square, or otherwise) to facilitate rotational advancement or retraction of the set screw relative to the connector 130 using a driver instrument. As shown in FIG. 1D, the degree to which the set screw recess 156 extends into the arms 152$a$, 152$b$ can differ between the first arm 152$a$ and the second arm 152$b$. Accordingly, when a rod 107 is seated against the distal extent 152$d$ of the second rod-receiving recess 152, the set screw axis A2 can be laterally offset from the central axis A4 of the rod 107. In other words, the connector 130 can be configured such that the set screw axis A2 does not intersect with the second rod axis A4.

The set screw 134 can thus be offset from the second rod 107 by curving or angling the rod-receiving recess 152, by shifting the set screw recess 156 relative to the rod-receiving recess 152, or, as shown in FIG. 1D, by a combination of both techniques. By offsetting the set screw 134 from second rod 107, the center-to-center offset between the first and second rods 106, 107 can be reduced while maintaining sufficient material in the arms 152$a$, 152$b$ for the set screw 134 to be securely fastened. Accordingly, optimal or desired rod placement can be achieved without compromising the structural integrity of the construct under the heavy anatomical loads encountered in the spine.

In the description above, the connector 130 is secured to the receiver member 104 using a cylindrical set screw 108 and a nut 132. It will be appreciated that other mechanisms can be used to attach the connector 130 to the receiver member 104. For example, FIGS. 2A-2E illustrate an exemplary connector assembly 200 that includes a locking spherical articulation joint. Except as described below or as will be readily appreciated by one having ordinary skill in the art, the structure and operation of the connector assembly 200 is substantially the same as that of the connector assembly 100 described above.

As shown, the opening 242 in the connector 230 can include an inner articulation surface 247. While the inner surface 247 can have various geometries, the illustrated surface 247 is spherical, e.g., defined by a section of a sphere. The assembly 200 can include a locking nut 260 configured to be received within the opening 242 of the connector 230. The locking nut 260 can include an outer articulation surface 249. While the outer surface 249 can have various geometries, the illustrated surface 249 is spherical, e.g., defined by a section of a sphere. The inner and outer surfaces 247, 249 can be complementary such that the locking nut 260 is polyaxially movable within the opening 242 relative to the connector 230. In some embodiments, the surfaces 247, 249 can have the same radius of curvature.

The locking nut 260 can be configured to expand and/or contract in a radial direction. For example, the locking nut 260 can include one or more slits 266 formed therein at which the locking nut 260 can be deformed to radially expand or contract. The illustrated locking nut 260 includes first and second diametrically opposed slits 266$p$ formed in a proximal surface 260$p$ thereof and first and second diametrically opposed slits 266$d$ formed in a distal surface 260$d$ thereof, though it will be appreciated that the locking nut 260 can include any number of slits formed in the proximal surface, the distal surface, or both. The slits 266$p$ formed in the proximal surface 260$p$ can be angularly offset relative to the slits 266$d$ formed in the distal surface 260$d$ about the circumference of the locking nut 260. For example, a 90 degree offset can be used as shown. The slits 266$p$ formed in the proximal surface 260$p$ can be used as a drive feature to receive a driver instrument for rotating the locking nut 260 about the set screw 208 to further thread the locking nut 260 onto the set screw 208.

Figure 2A:
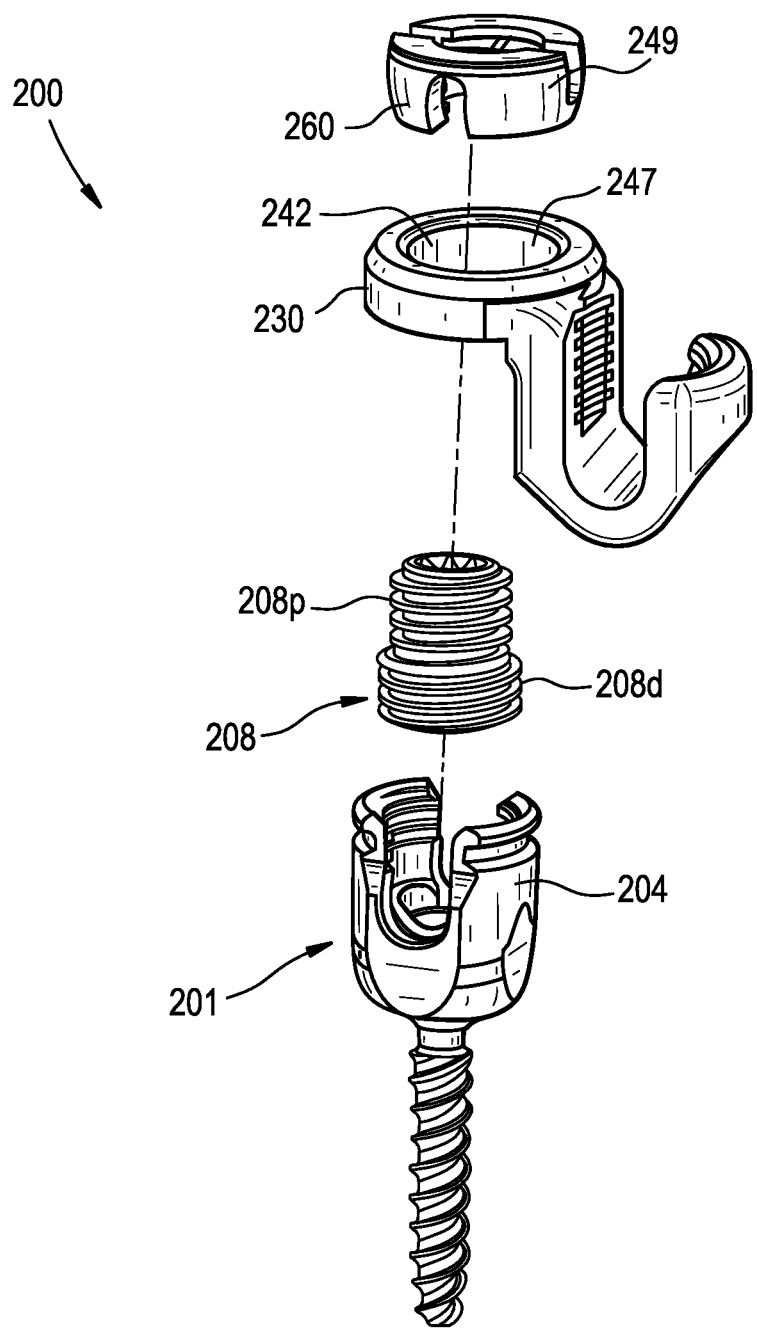
FIG. 2A is an exploded perspective view of connector assembly with a spherical articulation joint and shown with a bone anchor.
Figure 2B:
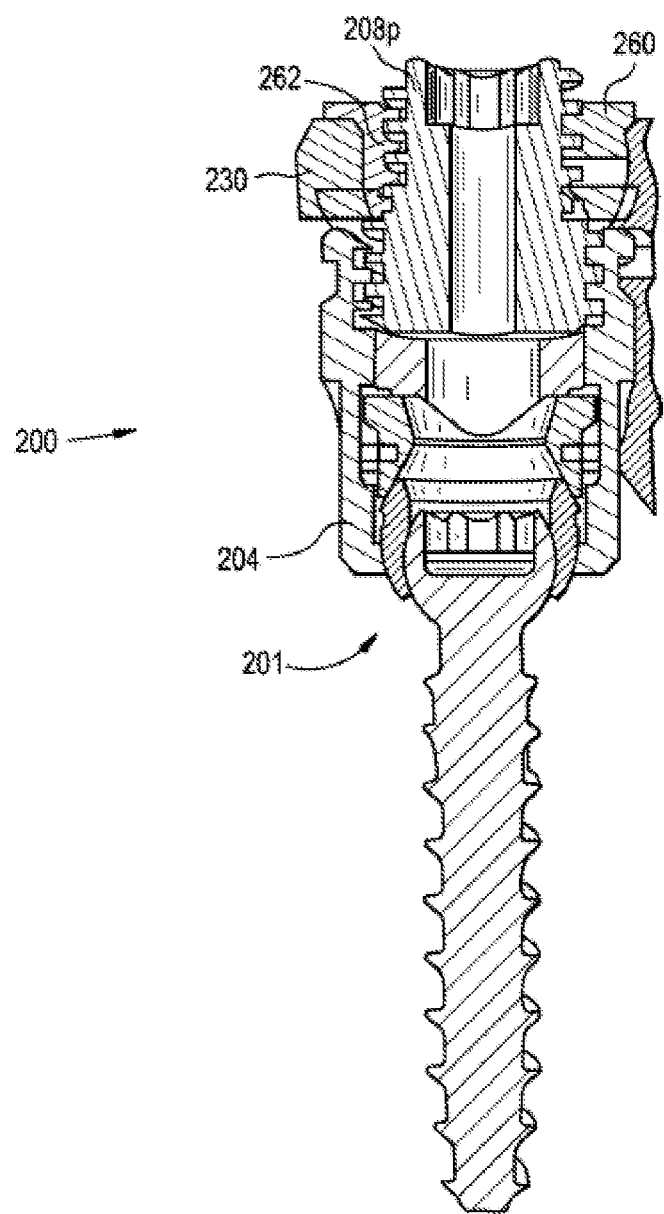
FIG. 2B is a sectional side view of the connector assembly and bone anchor of FIG. 2A.
Figure 2C:
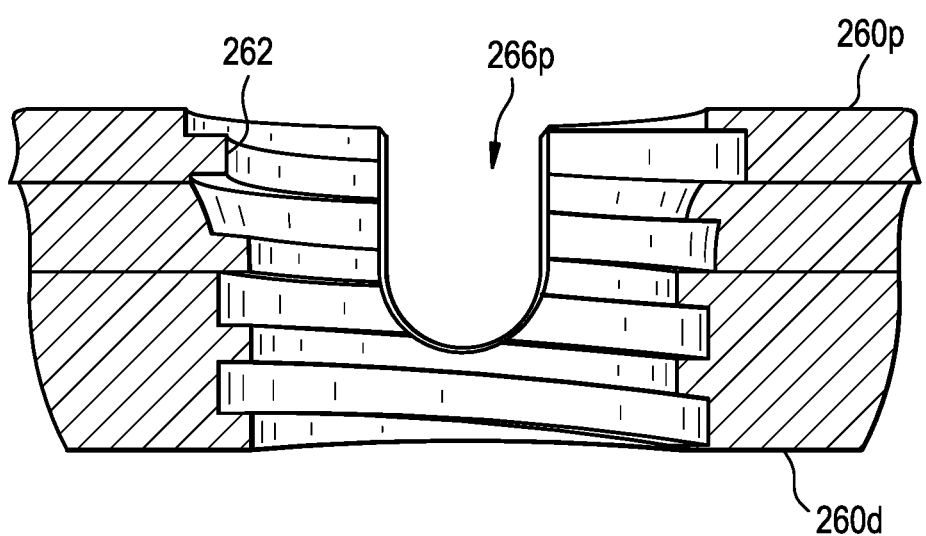
FIG. 2C is a sectional side view of a locking nut of the connector assembly FIG. 2A.

The locking nut 260 can include a threaded throughhole 262, shown for example in FIG. 2C, for threading the locking nut 260 onto the first set screw 208. The threads of the throughhole 262 and the threads of the set screw 208 can cooperate to cause radial expansion of the locking nut 260 as the locking nut is rotated in a first direction relative to the set screw and radial contraction of the locking nut as the locking nut is rotated in a second, opposite direction relative to the set screw. For example, the threads of the set screw 208 can be cylindrical and the threads of the locking nut 260 can be conical or tapered. As another example, the threads of the set screw 208 can be conical or tapered and the threads of the locking nut 260 can be cylindrical. The conical threads can taper at an angle of about 2 degrees to about 10 degrees from a rotation axis of the locking nut 260. The conical threads can taper at an angle of about 5 degrees to about 10 degrees from a rotation axis of the locking nut 260. The threads can have a tapered major diameter, a tapered minor diameter, or both.

In use, as discussed above, the set screw 208 can be disposed in the receiver member 204 of a bone anchor assembly 201 to secure a first rod (not shown) within the bone anchor assembly. The connector 230 can be located on the proximal end 208*p* of the set screw 208, for example, after the first rod is fixed within the receiver member 204. The locking nut 260 can be received within the opening 242 of the connector and at least partially threaded onto the set screw 208 to retain the connector 230 on the set screw. The assembly 200 can have a first, unlocked configuration in which the locking nut 260 is not tightened on the set screw 208 and is in a radially-contracted state to allow polyaxial movement of the connector 230 relative to the locking nut 260 and thus relative to the receiver member 204. The assembly 200 can also have a second, locked configuration in which the locking nut 260 is tightened onto the set screw 208 and is in a radially-expanded state to compress against the inner surface 247 of the opening 242 formed in the connector 230 to lock polyaxial movement of the connector 230 relative to the locking nut 260 and thus relative to the receiver member 204. The assembly 200 can also have intermediate states in which the locking nut 260 is partially tightened such that a drag force is applied to the connector 230, e.g., to allow provisional positioning of the connector to be maintained while still allowing movement when intended by the user.

Figure 2D:
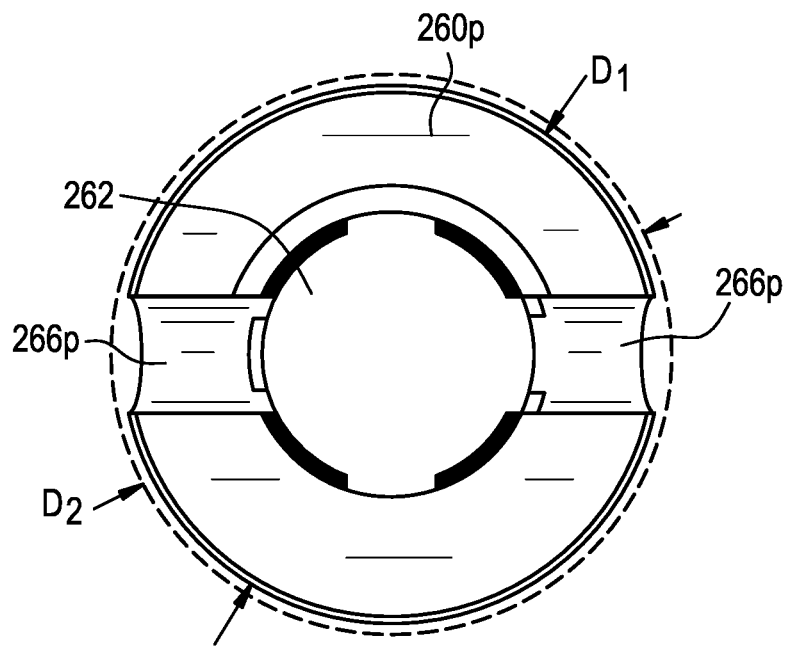
FIG. 2D is a top view of the locking nut of FIG. 2C.
Figure 2E:
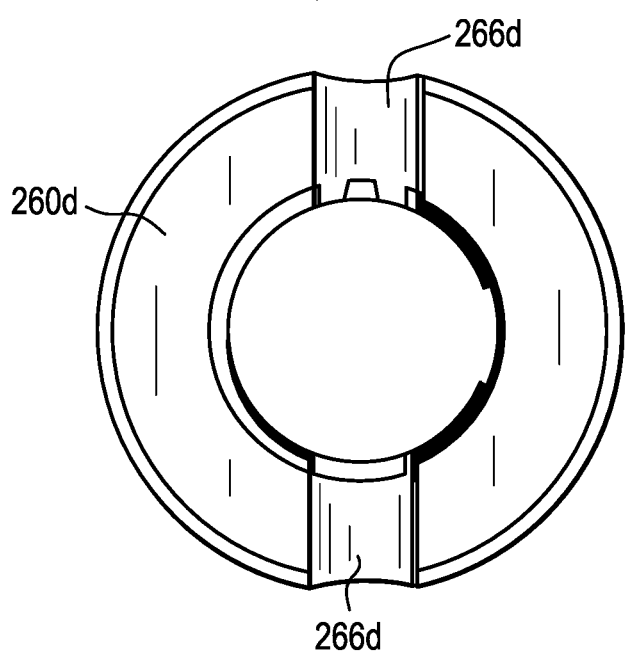
FIG. 2E is a bottom view of the locking nut of FIG. 2C.

As illustrated in FIG. 2D, in the unlocked configuration, the locking nut 260 can have a maximum outer diameter D1 that is sized to permit the connector 230 to polyaxially rotate about the locking nut 260. As illustrated in phantom in FIG. 2D, in the locked configuration, the locking nut 260 can have a maximum outer diameter D2 that is larger than the unlocked diameter D1. Accordingly, tightening the locking nut 260 onto the set screw 208 can be effective to create a compression fit between the connector 230 and the locking nut to lock the orientation of the connector relative to the receiver member 204. The locking nut 260 can be formed from any of a variety of known materials suitable for selective expansion and contraction. While slits 266 are shown, the locking nut 260 can be formed from a mesh material, can include a split extending completely therethrough, or can otherwise be configured to radially expand and contract without breaking.

The spherical articulation joint of the assembly 200 can serve as a ball joint, allowing for a range of articulation between the connector 230 and the receiver member 204. This can provide additional freedom in positioning the connector 230 relative to the first and second rods which can be helpful for example when the first and second rods are not parallel in any plane. The assembly 200 can allow for the locking and tightening functions of the articulation joint to be implemented in a single part, which can advantageously reduce the height profile of the construct within the wound.

The distal surface of the connector 230 can be shaped to enhance the degree to which the connector 230 can be angled relative to the receiver member 204, or to constrain movement of the connector relative to the receiver member in one or more directions, as described below with respect to FIGS. 3A-3D.

An alternative articulation joint is shown in FIGS. 3A-3D. For clarity of illustration, only the first portion 340 of the connector 330 is shown in FIGS. 3A-3D, it being appreciated that, in practice, the connector 330 would also include a second portion of the type described herein for receiving a second rod. The articulation joint of FIGS. 3A-3D is substantially the same as that of FIGS. 2A-2E, except as described below.

As shown, the locking nut 360 can have a truncated spherical shape having a proximal surface 360*p* and a distal surface 360*d*. The locking nut 360 can be sized and shaped to be polyaxially received within the opening 342 of the connector 330 to allow for polyaxial movement of the connector 330 with respect to the receiver member 304. The locking nut 360 can include a cut, or split, 366 extending from the proximal surface 360*p* to the distal surface 360*d*, and extending radially inward from the outer surface of the locking nut to a threaded throughhole 362. The split 366 can allow the locking nut 360 to expand or contract radially.

Figure 3A:
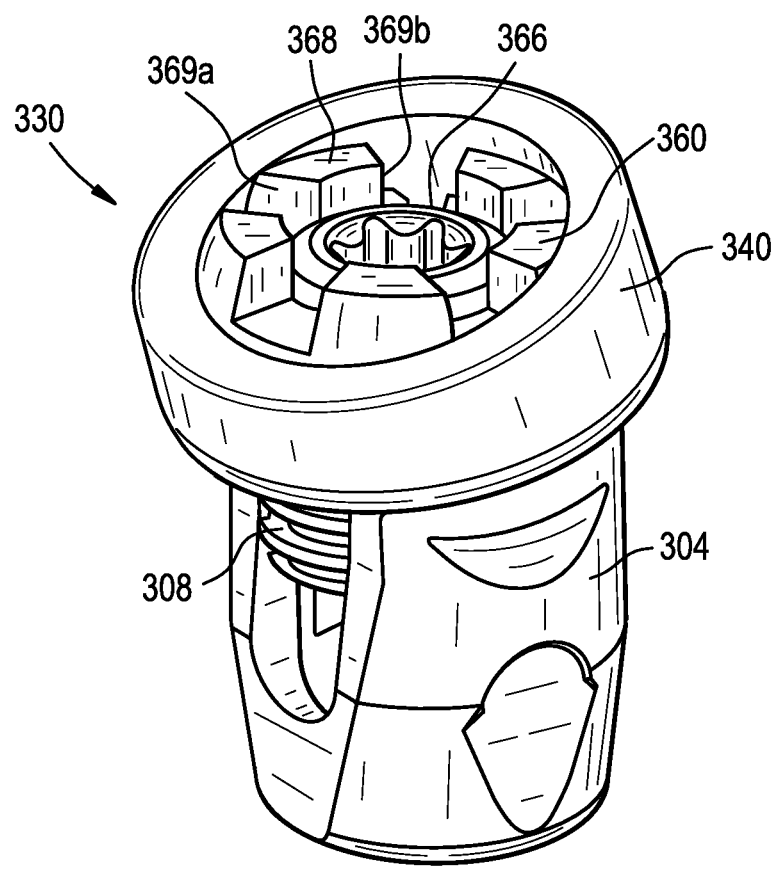
FIG. 3A is a partial perspective view of a connector assembly with a spherical articulation joint and shown with a bone anchor.
Figure 3B:
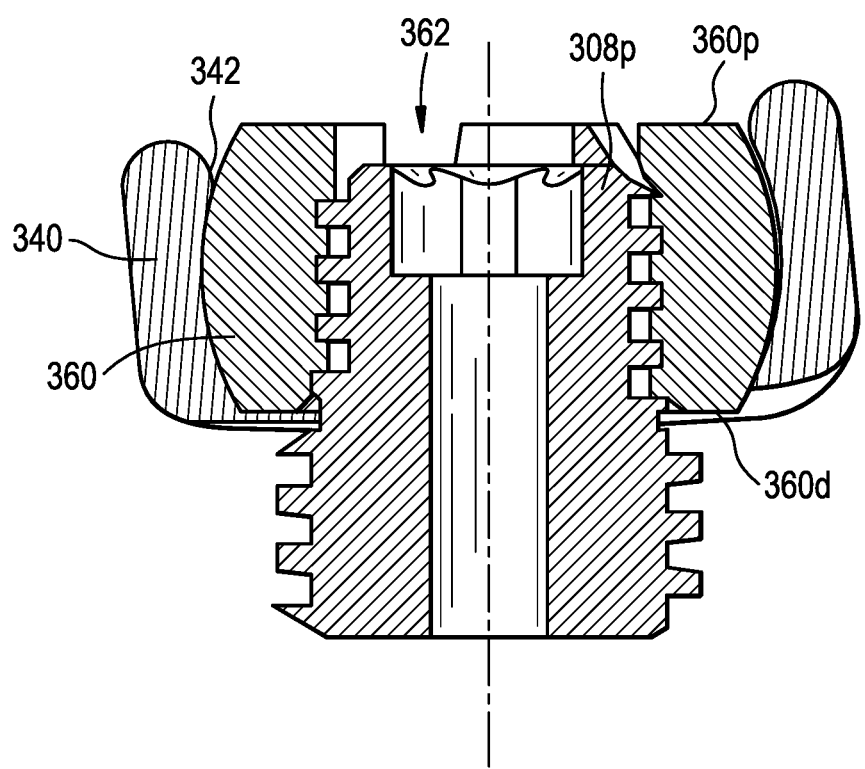
FIG. 3B is partial sectional side view of the connector assembly of FIG. 3A.
Figure 3C:
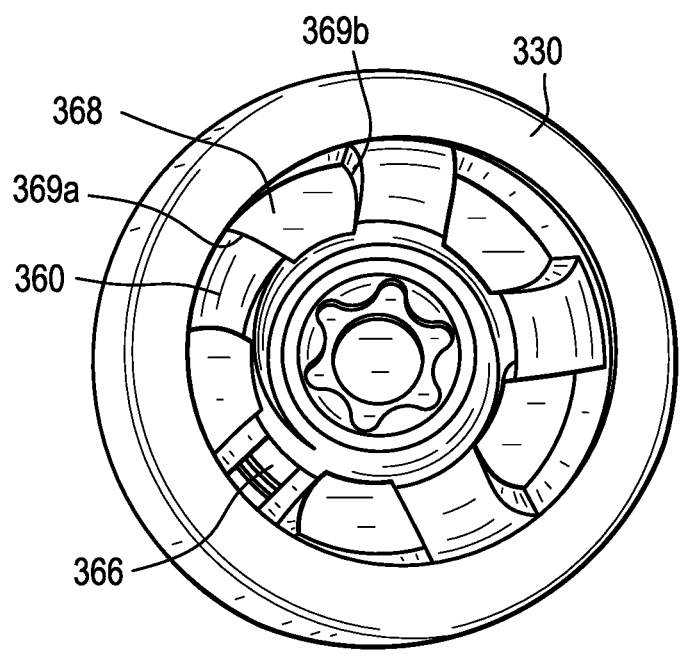
FIG. 3C is a top view of the connector assembly and bone anchor of FIG. 3A.

The locking nut 360 can include a castle-type drive feature defined by a plurality of projections 368 extending proximally from a proximal-facing surface 360*p* of the locking nut. Each projection can include a first abutment surface 369*a* and a second abutment surface 369*b*. The abutment surfaces 369*a*, 369*b* can allow for bidirectional application of torque to the locking nut 360 using a driver instrument. As shown in FIG. 3C, the first abutment surfaces 369*a*, the second abutment surfaces 369*b*, or both can be shaped to prevent binding with the driver instrument as the locking nut 360 expands and contracts. For example, the surfaces 369*a*, 369*b* can be convexly curved or can have rounded corners where the surfaces meet the exterior surface of the locking nut 360. As the locking nut 360 is expanded during tightening or contracted during loosening, the size of the castle drive feature likewise expands and contracts. By rounding the surfaces 369*a*, 369*b*, reliefs are provided to allow the driver instrument to be released and preventing binding or pinching of the driver instrument during such expansion or contraction.

Figure 3D:
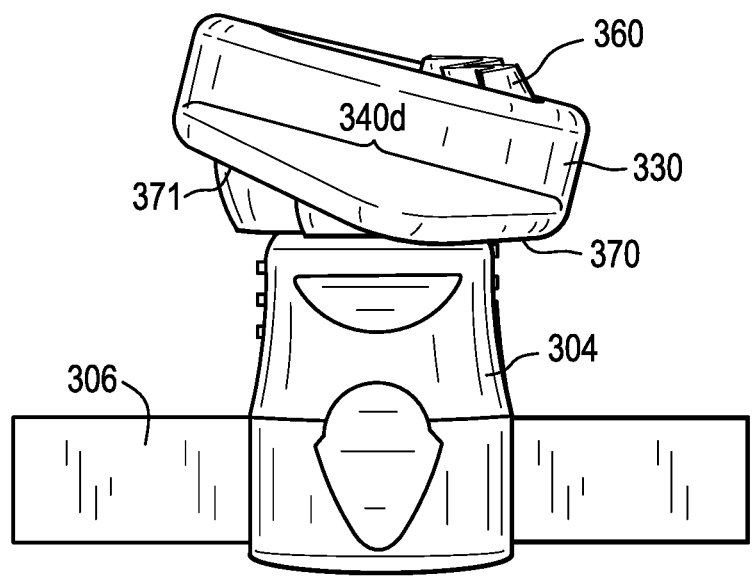
FIG. 3D is a partial side view of the connector assembly and bone anchor of FIG. 3A.

The distal surface 340*d* of the connector 330 can be shaped to enhance the degree to which the connector can be angled relative to the receiver member 304, or to constrain movement of the connector relative to the receiver member in one or more directions. For example, as shown in FIG. 3D, the distal surface 340*d* of the connector 330 can include a first generally planar region 370 and a second generally planar region 371 that extends obliquely from the first region. When positioned as shown in FIG. 3D, the first planar region 370 abuts the proximal-facing surface of the receiver member 304 to prevent pivoting movement of the connector 330 in a direction perpendicular to the first rod 306. The angled second portion 371, however, provides clearance between the distal surface 340*d* of the connector 330 and the proximal surface of the receiver member 304, allowing pivoting movement of the connector in a direction parallel to the first rod 306. It will be appreciated that, in other embodiments, the distal surface 340d of the connector 330 can be configured to allow pivoting perpendicular to the rod 306 and to prevent pivoting parallel to the rod, or to otherwise limit movement of the connector relative to the receiver member 304.

The outer surface of the locking nut 360 can be shaped to enhance the degree to which the connector 330 can be angled relative to the receiver member 304, or to constrain movement of the connector relative to the receiver member in one or more directions. For example, the outer surface can include one or more protrusions (not shown) formed thereon that interfere with movement of the connector 330 about the locking nut 360. The location of the one or more protrusions can be selected to limit connector movement in a desired direction or to a desired degree.

The connector assemblies herein can include various features for allowing or preventing certain movements of the connector relative to the receiver member.

Figure 4A:
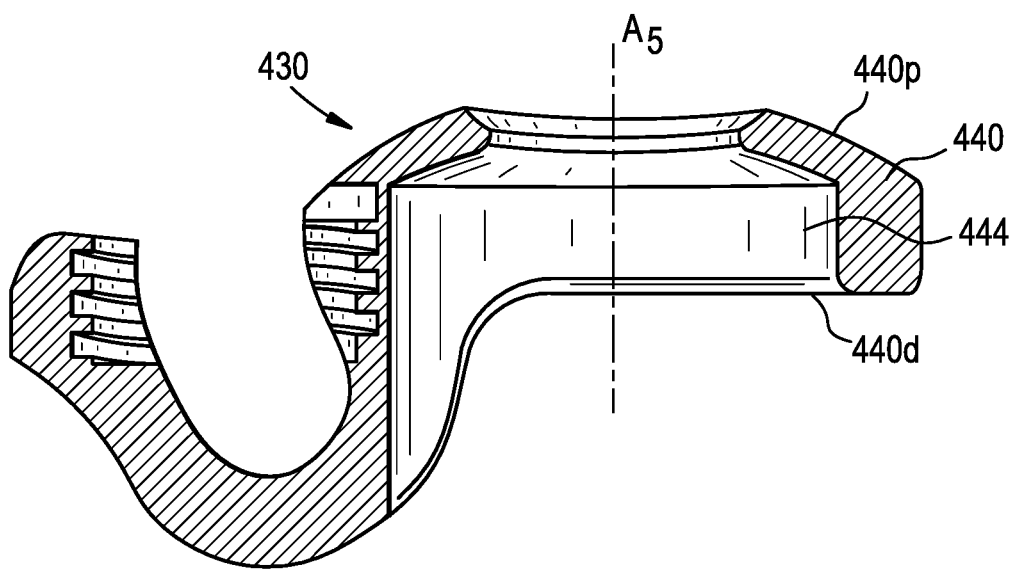
FIG. 4A is a sectional side view of a connector with a gimbal interface.
Figure 4B:
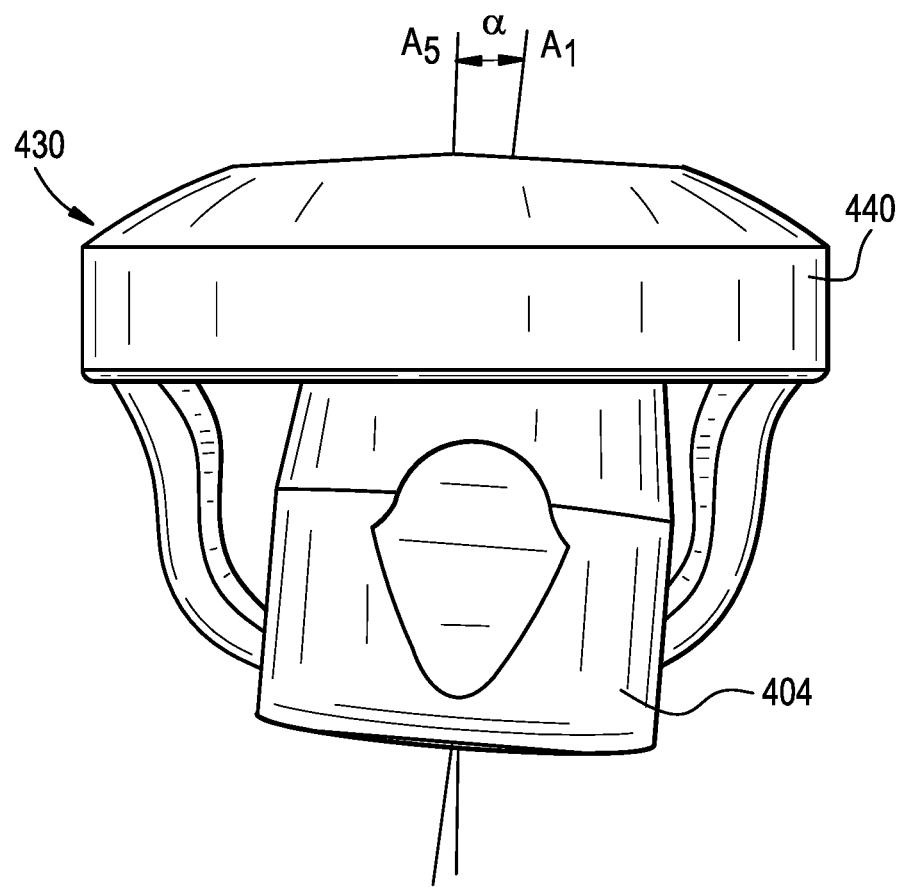
FIG. 4B is an end view of the connector of FIG. 4A shown with a bone anchor.
Figure 4C:
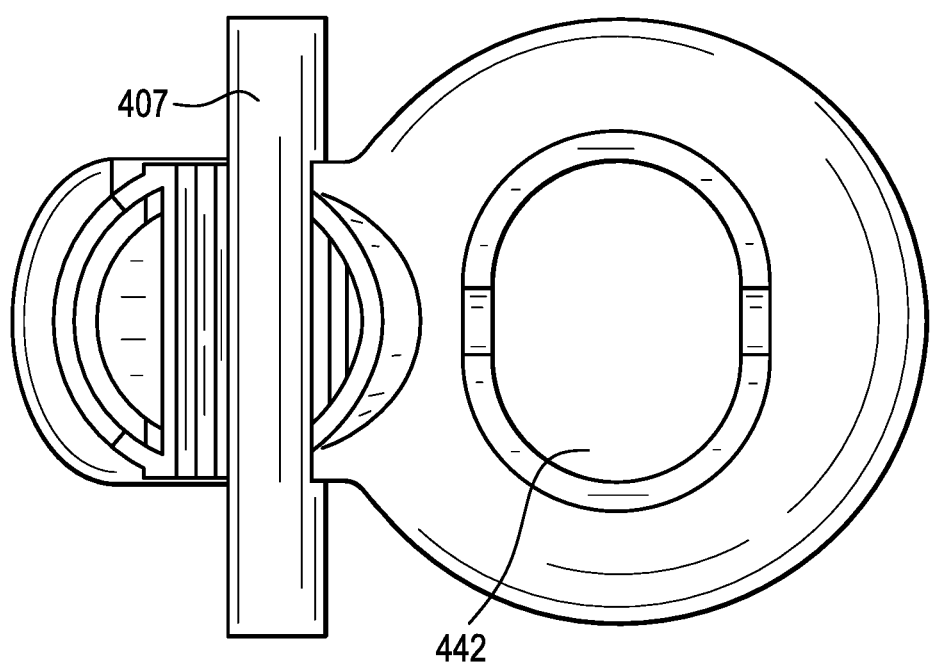
FIG. 4C is a top view of the connector of FIG. 4A.

For example, as shown in FIGS. 4A-4B, the connector 430 can mate with the receiver member 404 via a gimbal interface. The first portion 440 of the connector 430 can have a domed or spherical distal-facing surface 440d configured to bear against and slide across a corresponding domed or spherical proximal-facing surface of the receiver member 404. As shown in FIG. 4B, this can allow the connector 430 to move polyaxially over the receiver member 404, such that a central axis A5 of the connector opening 442 is obliquely angled with respect to a central axis A1 of the receiver member 404. The connector opening 442 can be oversized relative to the first set screw to allow relative movement between the connector 430 and the receiver member 404 when the connector is disposed over the set screw. The opening 442 can be oversized in all directions, for example by forming the opening with a diameter that is greater than the diameter of the set screw received therein. The opening 442 can also be oversized only in certain defined directions to limit movement of the connector 430 relative to the receiver member 404. For example, the opening 442 can be formed as an elongated slot as shown in FIG. 4C. The slot can be elongated in a direction parallel to the second rod 407 as shown, in a direction perpendicular to the second rod, or in any other desired direction. While the oversized or elongated opening 442 is described here in connection with a gimbal interface, it will be appreciated that the opening can be oversized, elongated, etc. even in embodiments that do not include a gimbal interface. When the connector 430 is positioned as desired, the nut can be tightened to lock the connector relative to the receiver member 404 at the desired position. The distal contacting surface of the nut can be concave to form a negative of or otherwise cooperate with the proximal surface 440p of the connector 430. The gimbal interface can allow for an angular offset a between the axis A1 and the axis A5. The geometry of the connector opening 442 and the set screw received therein can be selected to limit the maximum angulation of the connector relative to the receiver member 404. In some embodiments, the maximum angulation can range from about 2.5 degrees to about 45 degrees in any direction. In some embodiments, the maximum angulation can be about 7.5 degrees in any direction.

Figure 5A:
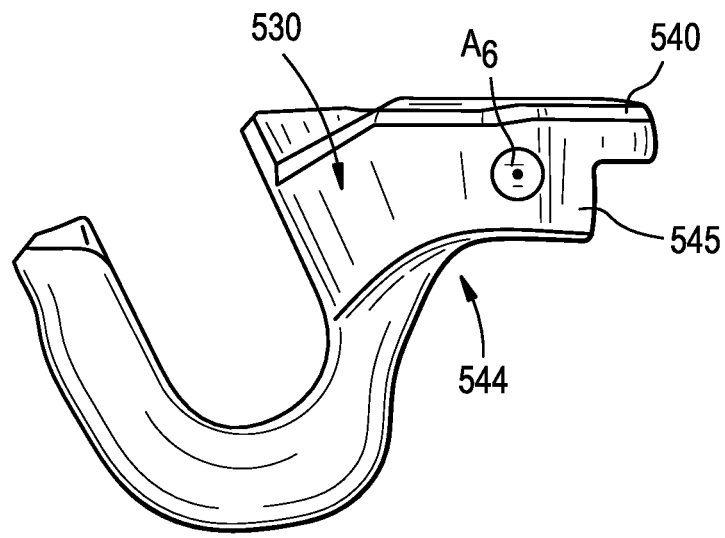
FIG. 5A is a side view of a connector with a sidewall for constraining movement of the connector relative to a bone anchor.
Figure 5B:
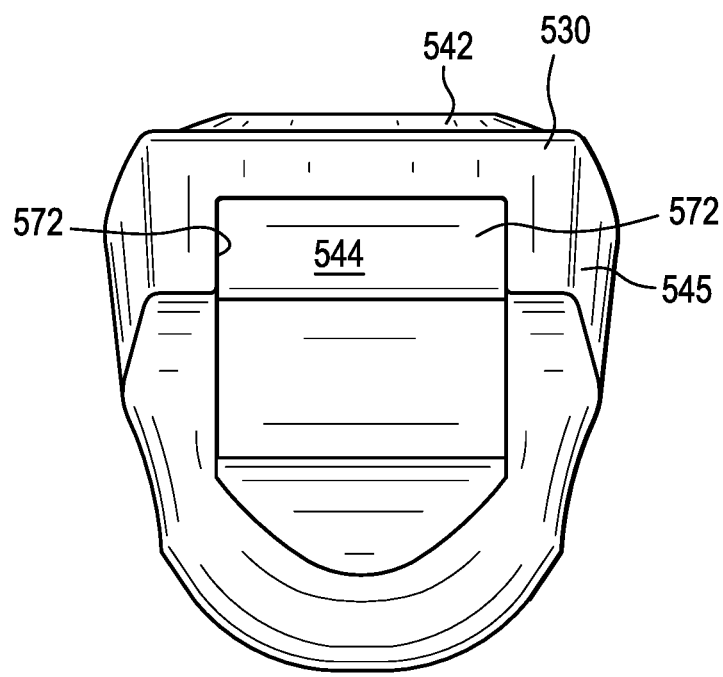
FIG. 5B is an end view of the connector of FIG. 5A.
Figure 5C:
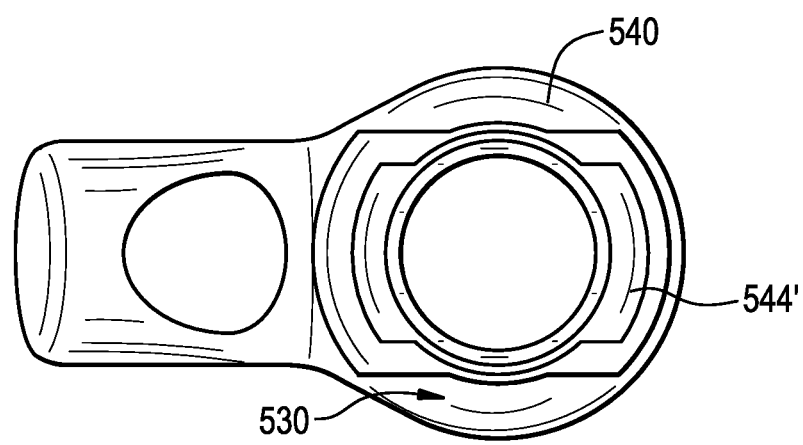
FIG. 5C is a bottom view of a connector with a recess for constraining movement of the connector relative to a bone anchor.

As another example, the distal end of the first portion of the connector can be configured to limit movement of the connector relative to the receiver member. As shown in FIGS. 5A-5B, the sidewall 545 of the first portion 540 of the connector 530 can have one or more flats 572 formed therein that cooperate with corresponding flats formed in the exterior surface of the receiver member to limit or prevent rotation of the connector relative to the receiver member about the axis A1. The sidewall 545 can be open at one or both ends of the connector 530 and the opening 542 can be elongated to allow the connector to pivot in a uniplanar manner with respect to the receiver member about an axis A6. This arrangement can be used, for example, when the user wishes to ensure that the first and second rods are parallel but desires the flexibility to adjust the relative proximal-distal height or center-to-center offset between the rods. As shown in FIG. 5C, the distal-facing surface 540d of the connector 530 can have a recess 544' formed therein that forms a negative of the proximal end of the receiver member. Accordingly, when the proximal end of the receiver member is received within the recess 544', the connector 530 cannot rotate or translate relative to the receiver member. This arrangement can be used, for example, when the user wishes to ensure that the first and second rods are parallel and disposed at a predetermined proximal-distal height relative to one another and at a predetermined center-to-center offset relative to one another.

By way of further example, the distal end of the first portion of the connector can include a positioner configured to selectively limit rotation of the connector relative to the receiver member about the axis A1. As shown in FIGS. 6A-6D, a positioner 660 can be disposed between the first portion 640 of the connector 630 and the receiver member 604. The positioner 660 can generally include a ring shaped body 662 and rotation resisting features 664a, 664b. The ring shaped body 662 can have a central opening 663 and proximal and distal surfaces 662p, 662d. The proximal surface 662p can include surface features 666 (e.g., teeth, a star grind, etc.). The distal surface 662d can include rotation resisting features such as spaced apart tabs 664a, 664b that project distally therefrom. The tabs 664a, 664b can be spaced apart to define a recess 665 therebetween for receiving the respective arms 604a, 604b of the receiver member 604. The tabs 664a, 664b can have a width that is substantially the same as the width of the recess 620 defined by the arms 604a, 604b of the receiver member. The tabs 664a, 664b can include a lip 668 that radially projects therefrom to aid in retaining the positioner 660 within the connector 630, as described further below.

Figure 6A:
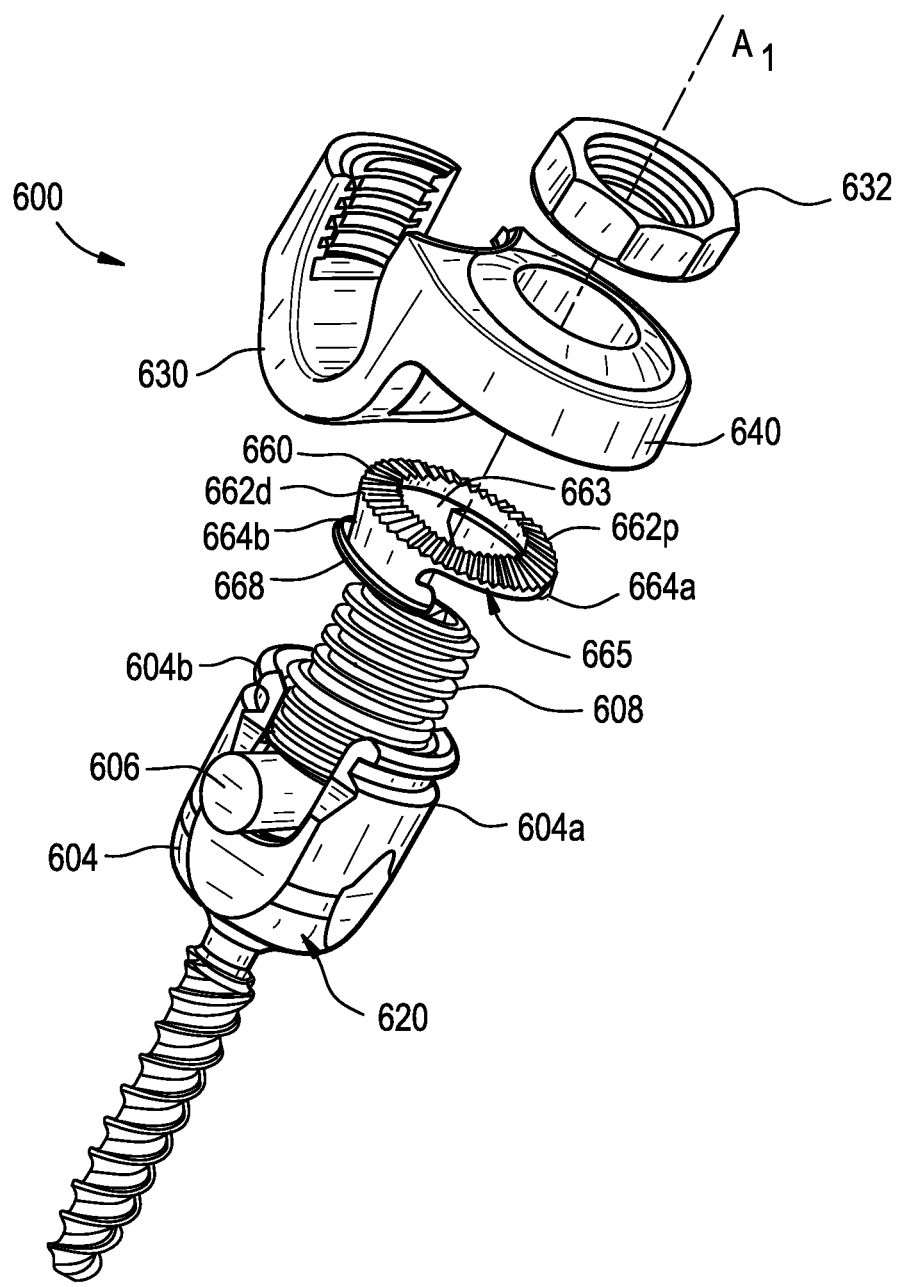
FIG. 6A is an exploded perspective view of a connector assembly shown with a bone anchor and a rod.
Figure 6B:
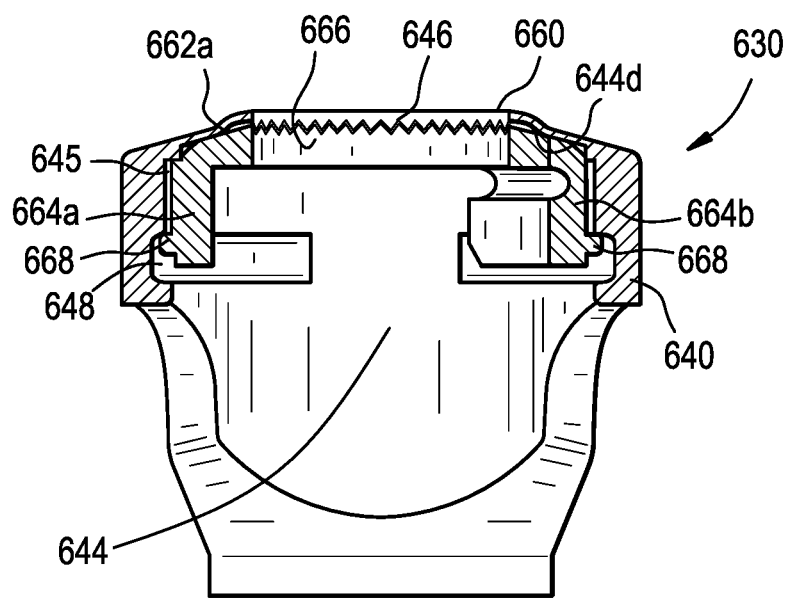
FIG. 6B is a sectional end view of a connector and a positioner of the connector assembly of FIG. 6A.
Figure 6C:
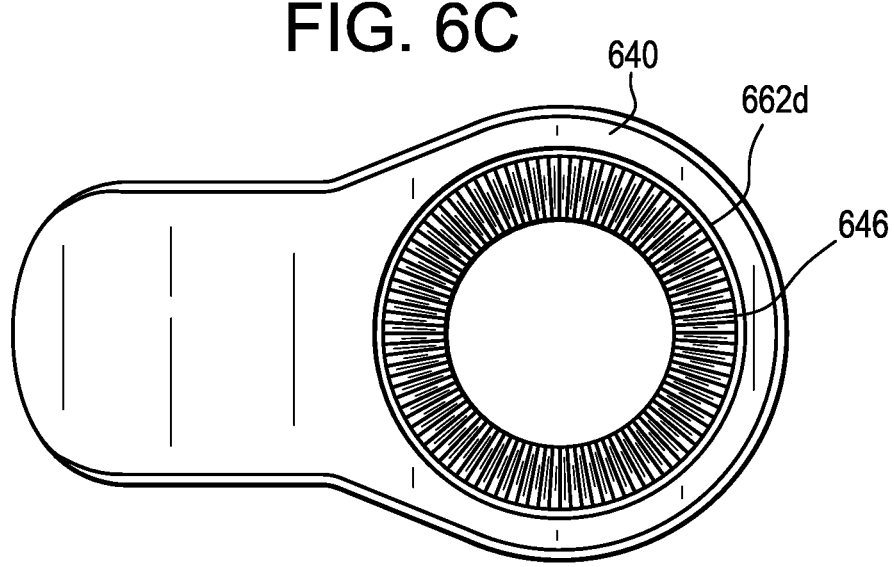
FIG. 6C is a bottom view of the connector of FIG. 6A.
Figure 6D:
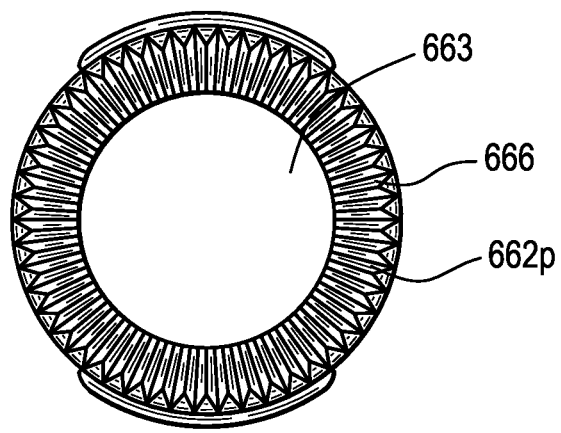
FIG. 6D is a top view of the positioner of FIG. 6A.

As shown in FIG. 6B, the first portion 640 of the connector 630 can include a recess 644 configured to receive the positioner 660. The recess 644 can include a distal facing surface 644d that includes surface features 646 (e.g., teeth, a star grind, etc.). The distal facing surface 644d can be configured such that the surface features 646 selectively bear against the surface features 666 of the proximal facing surface 662p of the positioner 660 as the construct is tightened. The recess 644 can include an annular groove 648 in the sidewall 645 of the recess. The annular groove 646 can be sized and shaped to receive the complementary lip 668 formed on the tabs 664a, 664b of the positioner 660 to retain the positioner 660 within the recess 644. The connector 630 and positioner 660 can, alternatively, be retained together by means of swaging, snapping, threading and other techniques. The connector 630 and the positioner 660 can form a subassembly that can be installed onto the set screw 608 as a single component. Alternatively, the connector 630 and the positioner 660 can be discrete components that are installed onto the set screw 608 individually, one at a time.

The positioner 660 and the connector 630 can be installed over the set screw 608 to rest atop the receiver member 604.

As the set screw 608 is placed through the central opening 663 of the positioner 660, the positioner 660 can be rotated about the set screw 608 to position the tabs 664a, 664b between the arms 604a, 604b of the receiver member 604 above the rod 606, and to position the arms 604a, 604b in the recesses 665 of the positioner 660. When the tabs 664a, 664b are disposed between the arms 604a, 604b of the receiver member 604 they can abut one another. The assembly 600, in this configuration, can prevent relative rotation between the positioner 660 and the receiver member 604 due to the tabs 664a, 664b abutting the arms 604a, 604b.

Before the nut, or other securing mechanism, 632 has been tightened to compress the assembly 600 together, the connector 630 and the positioner 660 can selectively rotate relative to each other about the axis A1. When the securing mechanism 632 is tightened, surface features 646, 666 on both the distally facing surface of the recess 644 and the proximal surface 662p of the positioner 660 can interact to selectively resist or prevent such rotation. The features of the connector 630 and the positioner 660 can be shaped such that they are complementary to each other and can be received within one another, as shown in FIG. 6B. The interaction between the surface features 646, 666 can, for example, eliminate the need for a counter torque instrument, e.g., when tightening the first set screw, the second set screw, or the nut, when securing the connector 630 on the receiver member 604. When the surface features 646 of the connector 630 engage, or are fit within, the surface features 666 of the positioner 660, the surface features 646, 666 can resist or prevent relative rotation about the axis A1.

Figure 7A:
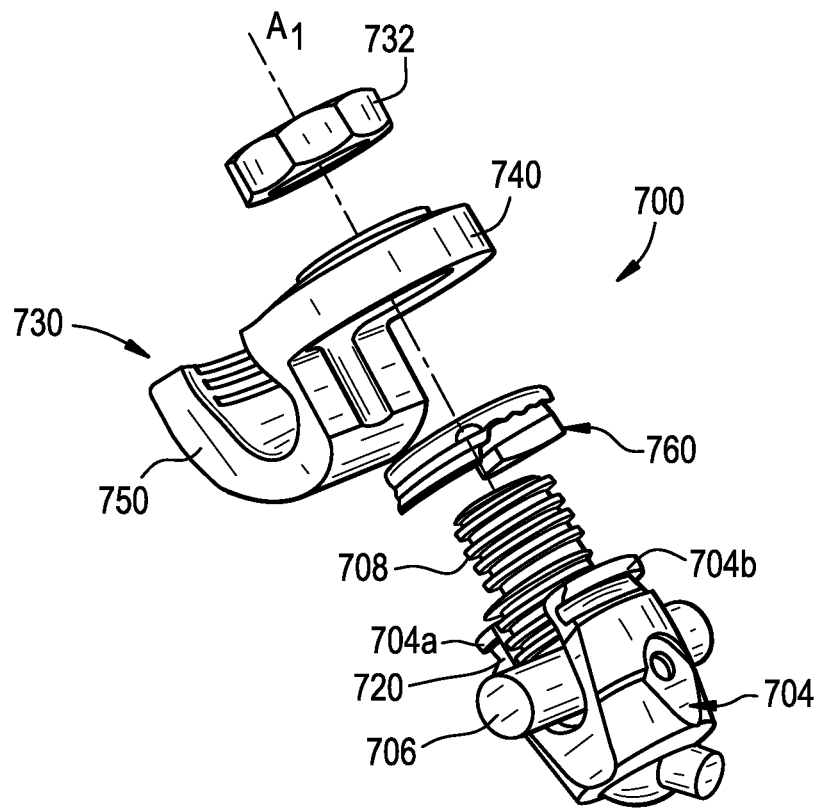
FIG. 7A is an exploded perspective view of a connector assembly shown with a bone anchor and a rod.
Figure 7B:
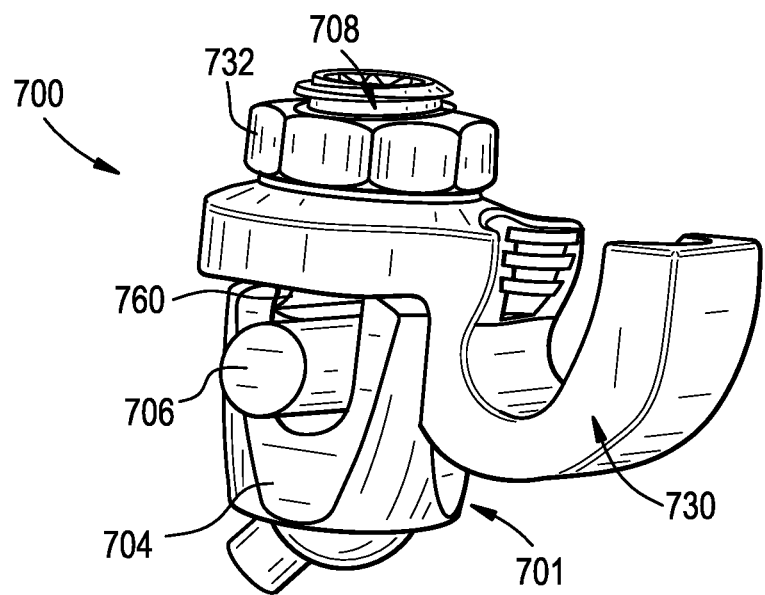
FIG. 7B is an assembled perspective view of the connector assembly, bone anchor, and rod of FIG. 7A.
Figure 7C:
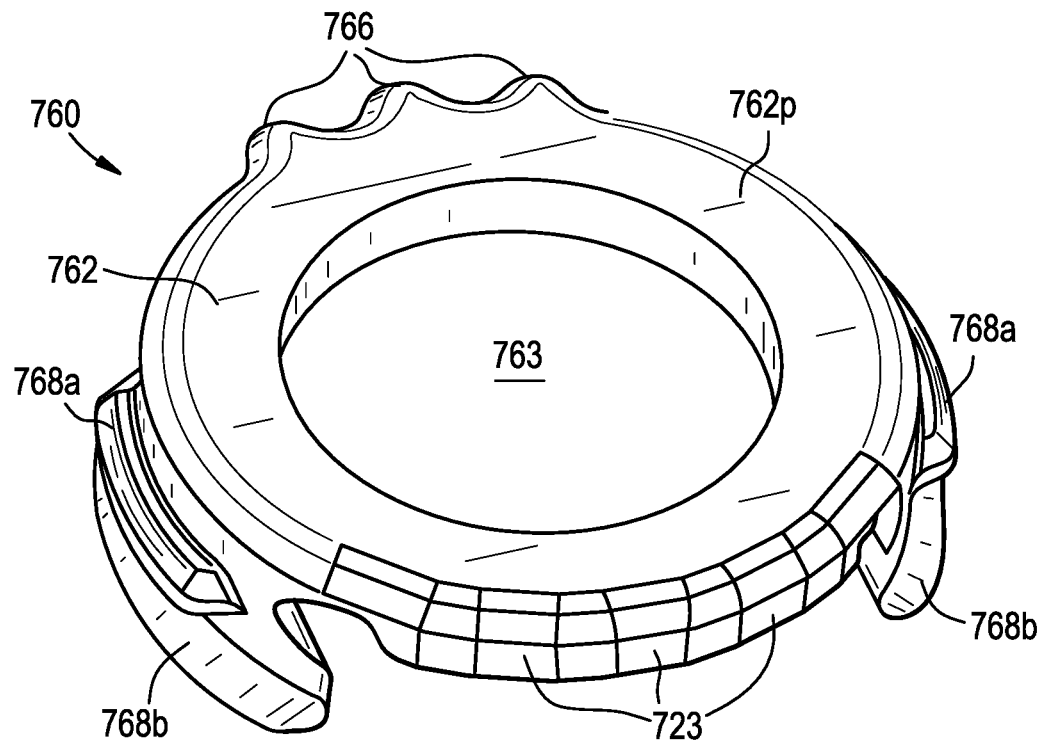
FIG. 7C is a perspective view of a positioner of the assembly of FIG. 7A.
Figure 7D:
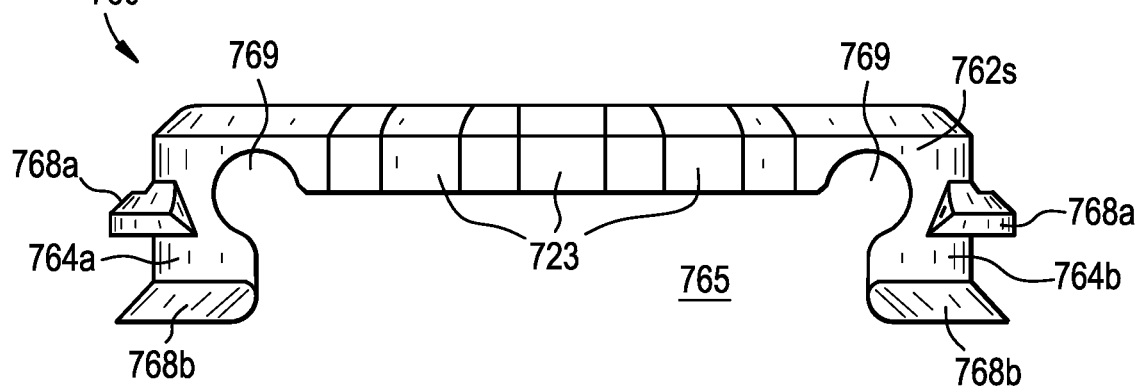
FIG. 7D is a side view of the positioner of FIG. 7C.
Figure 7E:
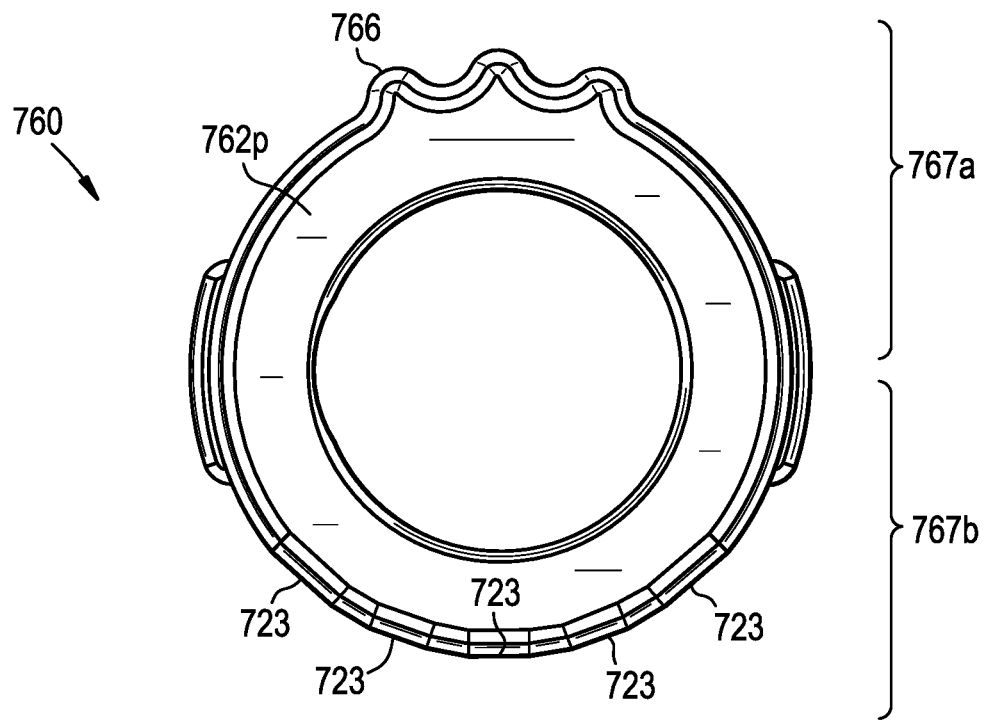
FIG. 7E is a top view of the positioner of FIG. 7C.

FIGS. 7A-7L illustrate another connector assembly 700 that includes a connector 730 and a positioner 760. Except as described below or as will be readily appreciated by one having ordinary skill in the art, the structure and operation of the connector assembly 700 is substantially the same as that of the connector assembly 600 described above. As shown in FIGS. 7A-7B, the positioner 760 can be configured to selectively limit rotation of the connector 730 relative to the receiver member 704 about the axis A1. The positioner 760 can be disposed between the first portion 740 of the connector 730 and the receiver member 704.

As shown in FIGS. 7C-7F, the positioner 760 can generally include a ring shaped body 762. The ring shaped body 762 can include a central opening 763, proximal and distal surfaces 762p, 762d, and an outer sidewall 762s. The body 762 can include a first hemisphere or first portion 767a and a second hemisphere or second portion 767b.

The positioner 760 can include rotation-resisting features configured to interact with the receiver member 704 to limit or prevent rotation between the positioner 760 and the receiver member 704 about the axis A1. For example, the positioner 760 can include spaced apart tabs 764a, 764b that project distally therefrom. The tabs 764a, 764b can be spaced apart to define recesses 765 therebetween for receiving the respective arms 704a, 704b of the receiver member 704. The tabs 764a, 764b can have a width that is substantially the same as the width of the channel 720 defined by the arms 704a, 704b of the receiver member 704. When inserted between the arms 704a, 704b of the receiver member 704, the tabs 764a, 764b can prevent rotation of the positioner 760 relative to the receiver member 704 about the axis A1.

Each tab 764a, 764b can include a first lip 768a that projects radially outward therefrom to aid in retaining the positioner 760 within the connector 730, as described further below. The first lip 768a can have a ramped, curved, or otherwise tapered proximal-facing lead-in surface to facilitate assembly with the connector 730. In particular, the tapered surface can allow the first lip 768a to ride over a ledge 725 of the connector 730 and snap-fit into a groove 748 formed in the connector 730.

Each tab 764a, 764b can include a second lip 768b that projects radially outward therefrom to engage the connector 730 during tightening and thereby clamp the positioner 760 onto the set screw 708, as described further below. The second lip 768b can have a ramped, curved, or otherwise tapered proximal-facing bearing surface. In some embodiments, the ramped surfaces of the second lips 768b can extend at an angle in the range of about 30 degrees to about 60 degrees from the horizontal. In some embodiments, the ramped surfaces of the second lips 768b can extend at an angle of about 45 degrees from the horizontal.

Cut-outs or other reliefs 769 can be formed at the junction between the tabs 764 and the body 762 to facilitate deflection or bending of the tabs towards and/or away from one another, e.g., during snap-fitting into the connector 730 or during clamping onto the set screw 708.

The positioner 760 can include features for selectively locking rotation between the positioner and the connector 730 about the axis A1. For example, the body 762 can include one or more teeth 766 projecting radially outward therefrom. The teeth 766 can engage or be enmeshed with corresponding teeth 729 formed in the connector 730 to lock rotation between the positioner 760 and the connector. While three teeth 766 are shown, it will be appreciated that the body 762 can include any number of teeth, or the teeth can be omitted altogether. The teeth 766 can be formed only in the first portion 767a of the body 762 as shown, or can be formed at any location about the circumference of the body. The surfaces of the teeth 766 that contact and bear against the teeth of the connector 730 can be rounded, chamfered, or otherwise shaped to facilitate release of the positioner 760 from the connector 730. This can advantageously help mobilize the construct when the assembly is loosened, e.g., to reposition the construct before final tightening.

As another example, the body 762 can include one or more flats 723 formed in the outer sidewall 762s of the body. Other than the teeth 766 and/or flat(s) 723, the outer sidewall 762s can be cylindrical. The flats 723 can engage or bear against one or more corresponding flats 727 formed in an inner sidewall 745 of the connector 730 to lock rotation between the positioner 760 and the connector. The flats 723 can be formed only in the second portion 767b of the body 762 as shown, or can be formed at any location about the circumference of the body. While flats are shown, it will be appreciated that the positioner 760 can include other eccentric features to perform a similar function, such as lobes, teeth, etc.

In some embodiments, both the first and second portions 767a, 767b of the body 762 can include teeth 766. In some embodiments, both the first and second portions 767a, 767b of the body 762 can include flats 723. In some embodiments, the first portion 767a of the body 762 can include teeth 766 and the second portion 767b of the body can include flats 723. In this arrangement, the positioner 760 can be oriented in the connector 730 such that the second portion 767b is adjacent to, or closer to, the rod slot of the connector. In some instances, to achieve the desired center-to-center offset of the first and second rods, the material thickness of the connector 730 adjacent to the rod slot of the connector may be limited such that use of teeth 766 in this area is impractical. Accordingly, flats 723 can be used in place of teeth on the second portion 767b of the positioner 760 such that the positioner 760 still includes rotation-preventing features on both the first portion 767a and the second portion 767b, even when the material thickness of the connector is limited.

Figure 7F:
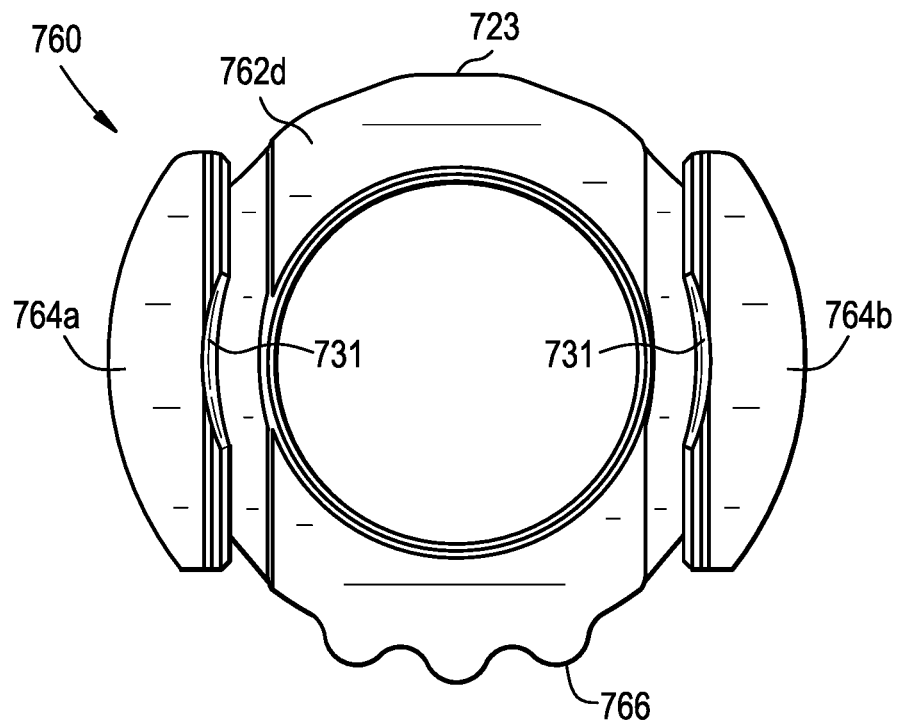
FIG. 7F is a bottom view of the positioner of FIG. 7C.
Figure 7G:
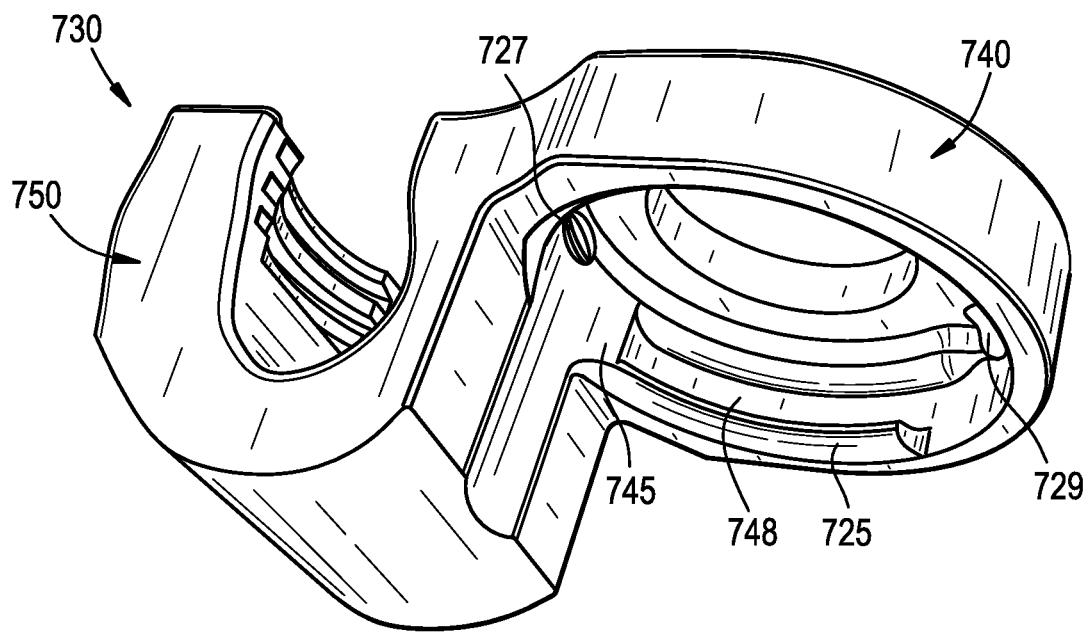
FIG. 7G is a perspective view of a connector of the assembly of FIG. 7A.
Figure 7H:
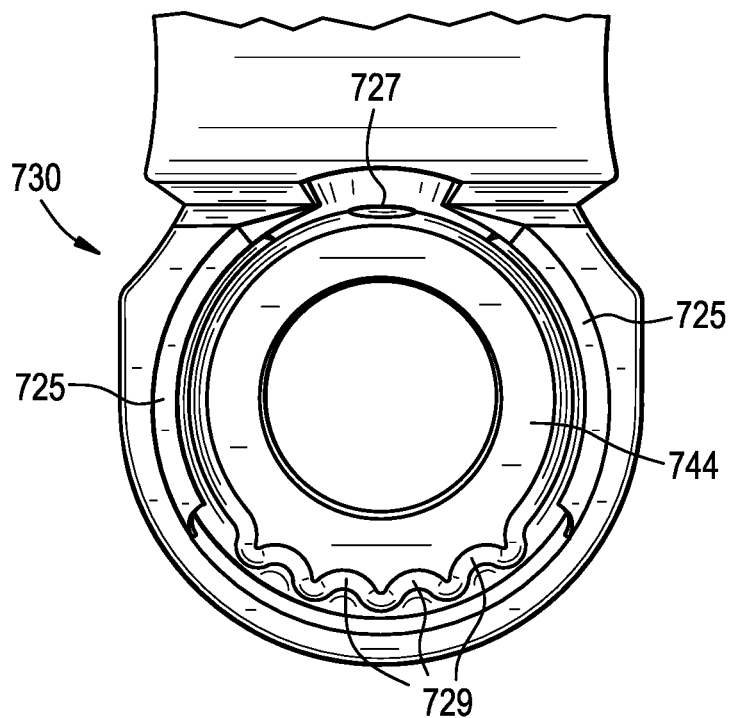
FIG. 7H is a partial bottom view of the connector of FIG. 7G.

The connector 730 is shown in more detail in FIGS. 7G-7H. The connector 730 can include a first portion 740 for mating the connector with a bone anchor assembly 701 and a second portion 750 for mating the connector with a fixation element such as an elongate spinal rod. The illustrated second portion 750 is exemplary, and the connector 730 can include any of the second portions described herein. The first portion 740 of the connector 730 can include a recess 744 configured to receive the positioner 760. The recess 744 can be defined at least in part by a sidewall 745. A groove 748 can be formed in the sidewall 745 and can define a distal ledge 725. The groove 748 can be sized and shaped to receive the first lips 768a of the positioner 760 to retain the positioner within the recess 744. The ledge 725 can define a ramped, curved, or otherwise tapered distal-facing lead-in surface. In some embodiments, the ramped surface of the ledge 725 can extend at an angle in the range of about 30 degrees to about 60 degrees from the horizontal. In some embodiments, the ramped surface of the ledge 725 can extend at an angle of about 45 degrees from the horizontal.

As the positioner 760 is advanced proximally into the connector 730, the tapered proximal-facing surface of the first lips 768a can ride over the tapered distal-facing surface of the ledge 725 to deflect the arms 764 of the positioner inward until the positioner is advanced more proximally and the first lips 768a snap-fit into the groove 748. The first lips 768a can be configured to slide within the groove 748 such that the positioner 760 can rotate within the connector 730 prior to tightening the assembly 700. The degree to which the positioner 760 can rotate within the connector 730 prior to tightening can be limited. For example, as shown, the groove 748 can extend along less than the entire inner circumference of the sidewall 745. The illustrated groove 748 terminates at or near the 11 o'clock and 1 o'clock positions in FIG. 7H. The terminations of the groove 748 can define stop surfaces configured to contact the first lips 768a to limit rotation of the positioner 760 within the connector 730. The groove 748 can have a height along the axis A1 that is greater than a corresponding height of the lips 768a such that a limited amount of axial travel of the positioner 760 relative to the connector 730 along the axis A1 is permitted before the assembly 700 is tightened.

While a snap-fit arrangement is shown, the connector 730 and positioner 760 can, alternatively, be retained together by means of swaging, snapping, threading and other techniques. The connector 730 and the positioner 760 can form a subassembly that can be installed onto the set screw 708 as a single component. Alternatively, the connector 730 and the positioner 760 can be discrete components that are installed onto the set screw 708 individually, one at a time.

The connector 730 can include features for engaging or otherwise interacting with the teeth 766 and/or flats 723 of the positioner 760. For example, the inner sidewall 745 of the connector 730 can include one or more flats 727 configured to mate with the flats 723 of the positioner 760. While a single flat 727 is shown at the 12 o'clock position in FIG. 7H, it will be appreciated that the connector 730 can include any number of flats 723 at any of a variety of positions along the sidewall 745. As another example, the inner sidewall can include one or more teeth 729 configured to mate with the teeth 766 of the positioner 760. The teeth 729 can project radially-inward from the sidewall 745. The teeth 729 can engage or be enmeshed with corresponding teeth 766 of the positioner 760 to lock rotation between the positioner 760 and the connector 730. While four teeth 729 are shown, it will be appreciated that the connector 730 can include any number of teeth, or the teeth can be omitted altogether. The surfaces of the teeth 729 that contact and bear against the teeth 766 of the positioner 760 can be rounded, chamfered, or otherwise shaped to facilitate release of the positioner 760 from the connector 730. This can advantageously help mobilize the construct when the assembly is loosened, e.g., to reposition the construct before final tightening. Such surface features can also facilitate alignment of the teeth 766, 729 as the construct is tightened.

The positioner 760 and the connector 730 can be installed over the set screw 708 to rest atop the receiver member 704. As the set screw 708 is placed through the central opening 763 of the positioner 760, the positioner 760 can be rotated about the set screw 708 to position the tabs 764a, 764b between the arms 704a, 704b of the receiver member 704 above the rod 706, and to position the arms 704a, 704b in the recesses 765 of the positioner 760. When the tabs 764a, 764b are disposed between the arms 704a, 704b of the receiver member 704 they can abut one another. The assembly 700, in this configuration, can prevent relative rotation between the positioner 760 and the receiver member 704 due to the tabs 764a, 764b abutting the arms 704a, 704b.

Figure 7I:
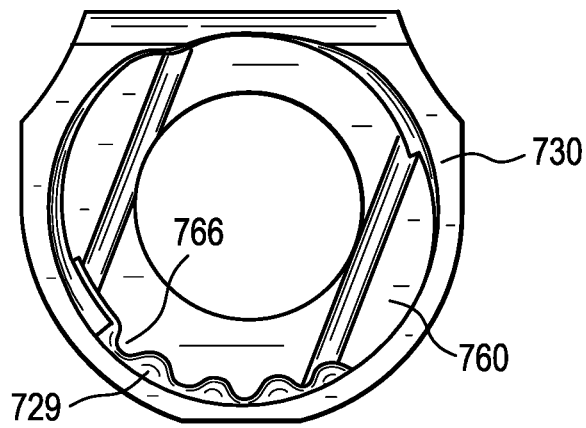
FIG. 7I is a partial bottom view of the connector and the positioner of FIG. 7A in a first configuration.
Figure 7J:
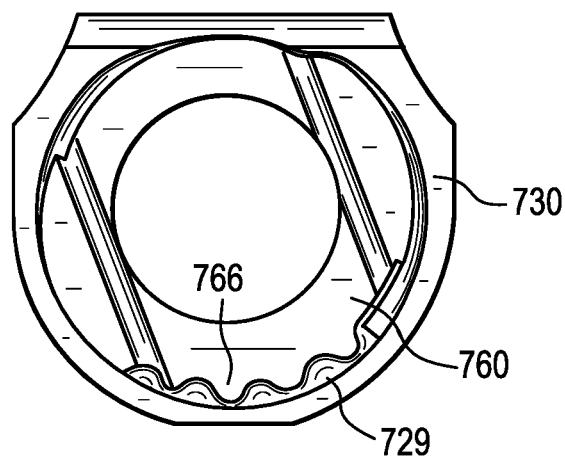
FIG. 7J is a partial bottom view of the connector and the positioner of FIG. 7A in a second configuration.
Figure 7K:
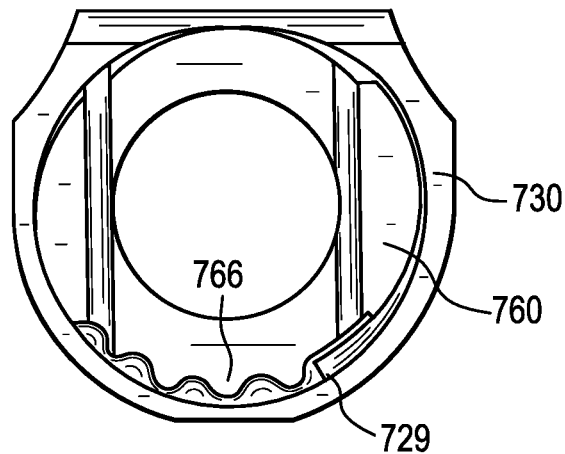
FIG. 7K is a partial bottom view of the connector and the positioner of FIG. 7A in a third configuration.

Before the nut, or other securing mechanism, 732 has been tightened to compress the assembly 700 together, the connector 730 and the positioner 760 can rotate relative to each other about the axis A1. When the securing mechanism 732 is tightened, the teeth 766, 729 can become enmeshed to resist or prevent such rotation. The flats 723, 727 can likewise engage with one another when the nut 732 is tightened to provide further resistance to rotation between the connector 730 and the positioner 760. As shown in FIGS. 7I-7K, interaction between the teeth 729, 766 and interaction between the flats 723, 727 can allow the positioner 760 to be placed and locked in any of a plurality of discrete rotational positions relative to the connector 730. Accordingly, by extension, the connector 730 can be placed and locked in any of a plurality of discrete rotational positions relative to the receiver member 704. As noted above, in some embodiments, the assembly can include teeth only, flats only, or neither teeth nor flats. In the latter arrangement, locking can be achieved by frictional engagement between the proximal surface of the positioner and the distal surface of the connector when the nut 732 is tightened. In this arrangement, the positioner can be positioned in any of an infinite number of rotational positions relative to the connector.

Figure 7L:
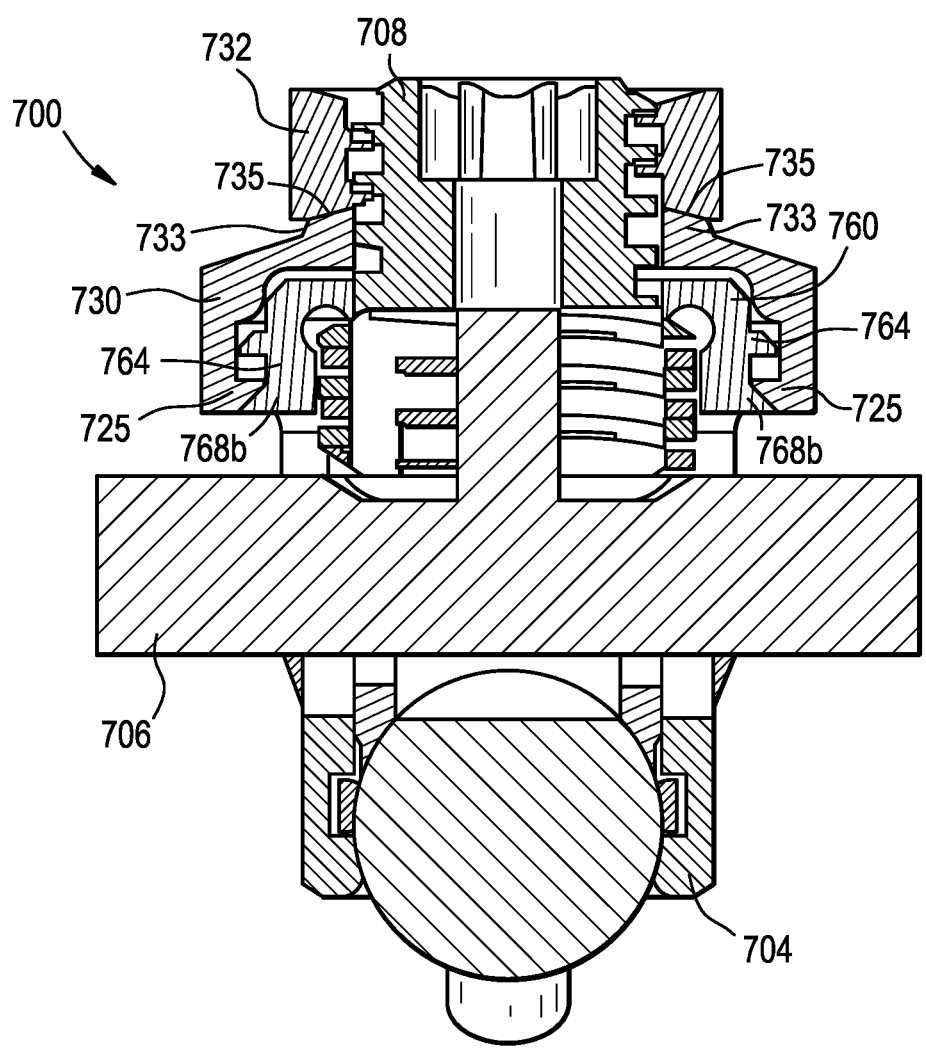
FIG. 7L is a sectional end view of the connector assembly of FIG. 7A, a bone anchor, and a rod.

As shown in FIG. 7L, as the nut 732 is tightened, the connector 730 can move distally along the set screw 708 towards the receiver member 704. The positioner 760 can be constrained from advancing distally due to interference from at least one of the set screw 708, the receiver member 704, and the rod 706. As the connector 730 advances distally along the screw 708 relative to the positioner 760, the ramped distal-facing surface of the ledge 725 can bear against the ramped proximal-facing surface of the second lips 768b of the positioner 760. This can cause the tabs 764 of the positioner 760 to deflect radially inward and to clamp onto the set screw 708. This clamping engagement between the positioner 760 and the set screw 708 can strengthen the overall assembly and reduce or eliminate any play or toggle between components. The tabs 764 can engage a non-threaded portion of the set screw 708, e.g., one or more flats formed in the sidewall of the set screw. The tabs 764 can include arcuate reliefs or cut-outs 731, e.g., as shown in FIG. 7F, to provide relief for the set screw 708 threads and to help ensure that the arms 764 clamp only onto the unthreaded and/or flat portion of the set screw.

The assembly 700 can include features to help ensure consistent and efficient tightening torque when tightening the nut 732. For example, as shown in FIG. 7L, the proximal surface of the connector 730 can include a raised protrusion 733. The protrusion 733 can define a proximal-facing contact surface, which can be ramped, curved, or otherwise tapered. In the illustrated embodiment, the protrusion 733 defines a male conical surface. The nut 732 can include a complementary distal-facing contact surface 735 which can be ramped, curved, or otherwise tapered. In the illustrated embodiment, the contact surface 735 of the nut 732 defines a female conical surface. It will be appreciated that, in other arrangements, the connector 730 can include a female surface and the nut 732 can include a male surface. The angles of the respective contact surfaces can be the same or can be different. For example, when viewed in cross-section, the distal-facing surface of the nut 732 can extend from the horizontal at an angle of about 30 degrees and the proximal-facing surface of the protrusion 733 can extend from the horizontal at an angle of about 35 degrees. When the nut 732 and the protrusion 733 define different angles as shown, friction between the two mating surfaces can spread inside-to-out in a radial direction away from the set screw axis as the construct is tightened. This can help ensure controlled, evenly-increasing friction as the nut is tightened, leading to consistent and efficient tightening torque. Any of the connector assemblies disclosed herein can include features of this type.

The connector assembly can include various features for positioning the second rod at a desired proximal-distal height relative to the first rod.

Figure 8:
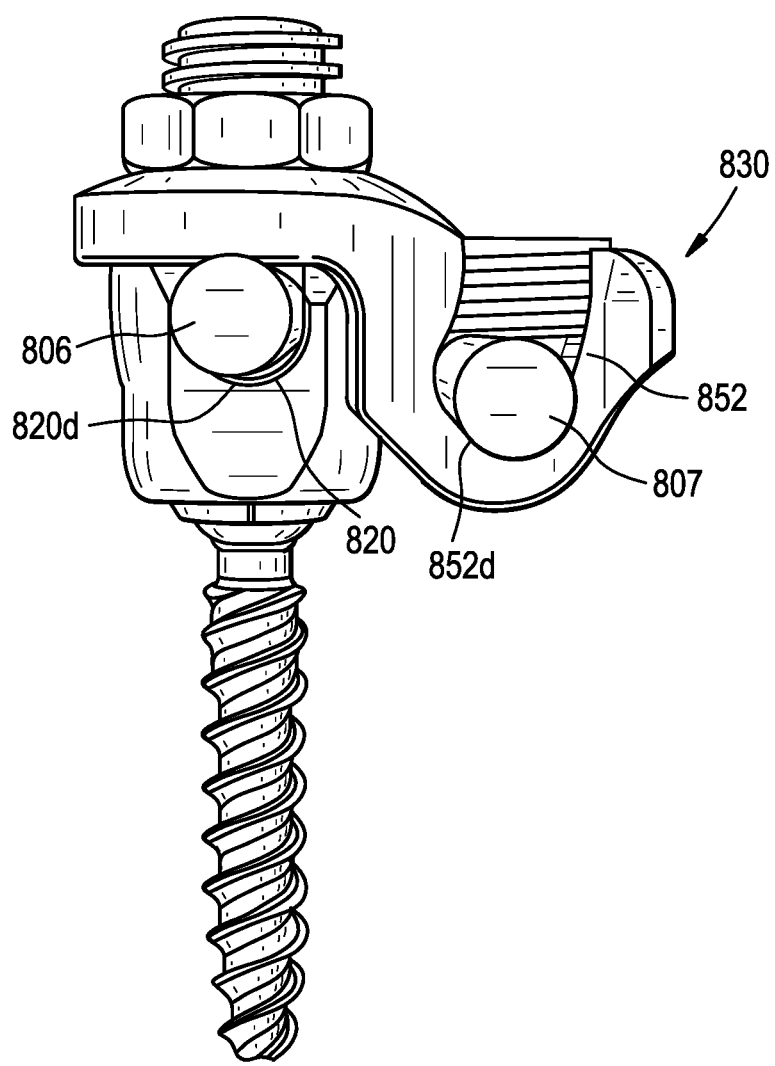
FIG. 8 is a side view of a connector assembly shown with a bone anchor and first and second rods.

For example, as shown in FIG. 8, the second rod-receiving recess 852 can be elongated in the proximal-distal direction to allow the second rod 807 to be positioned distal to the first rod 806. In other words, the connector 830 can be used to position the second rod 807 anterior to the first rod 806 when the assembly is attached to the posterior aspects of a patient's spine. As shown, the second rod-receiving recess 852 can extend to a distal most rod seat 852d that is more distal than the rod seat 820d of the first rod-receiving recess 820.

Figure 9A:
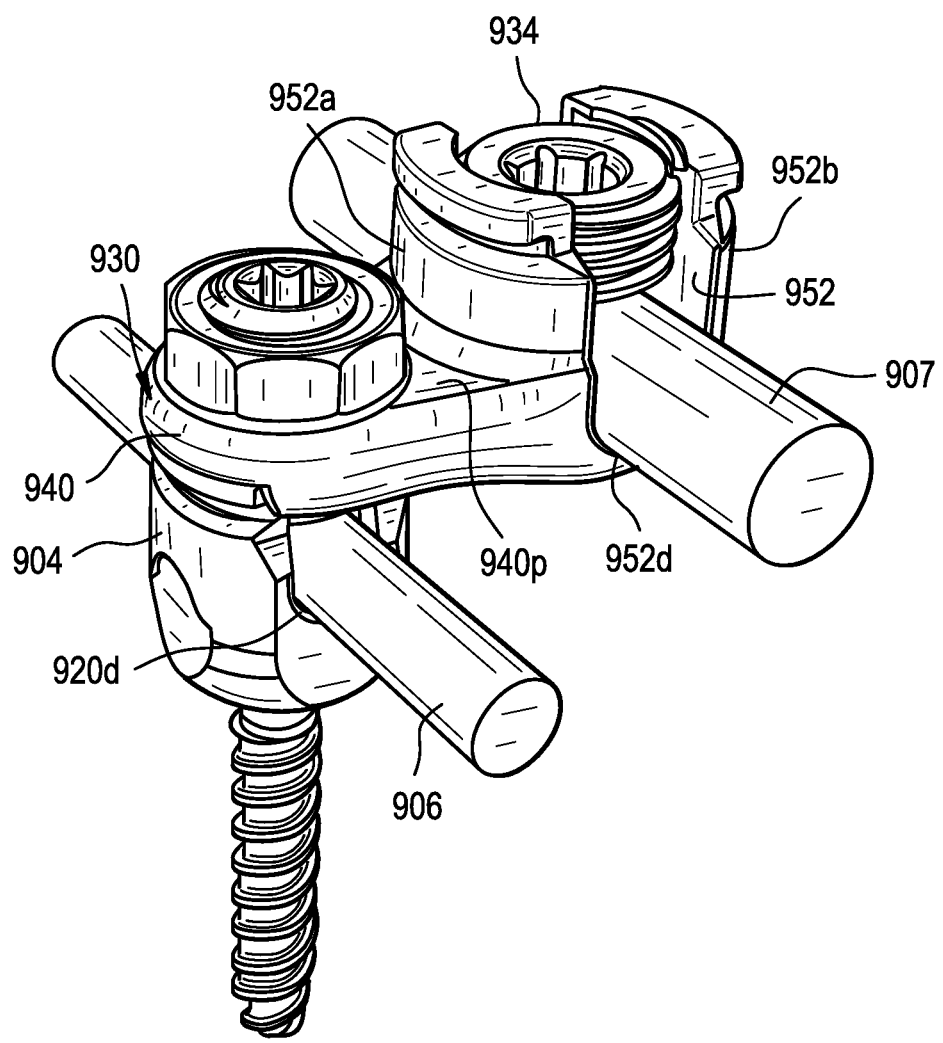
FIG. 9A is a perspective view of a connector assembly shown with a bone anchor and first and second rods.
Figure 9B:
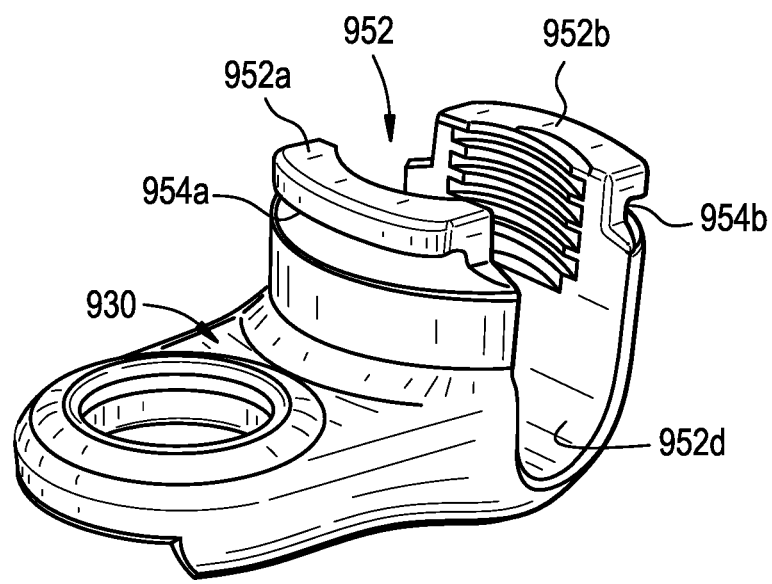
FIG. 9B is a perspective view of a connector of the connector assembly of FIG. 9A.
Figure 9C:
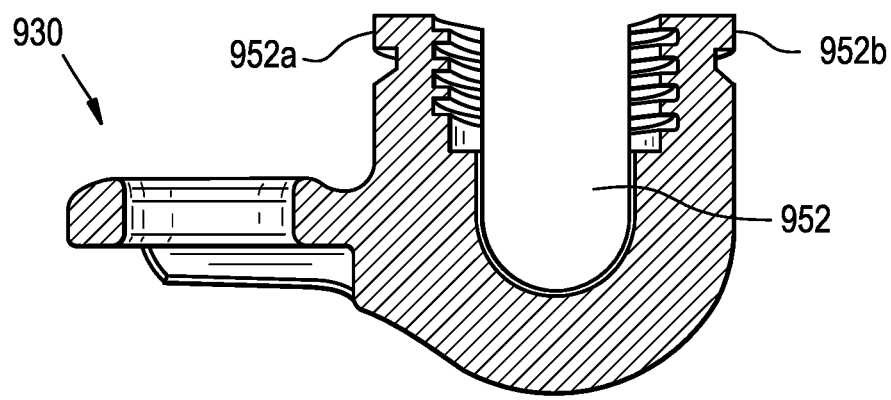
FIG. 9C is a sectional side view of the connector of FIG. 9B.

By way of further example, as shown in FIGS. 9A-9C, the connector 930 can be configured to position the second rod 907 proximal to the first rod 906. In other words, the connector 930 can be used to position the second rod 907 posterior to the first rod 906 when the assembly is attached to the posterior aspects of a patient's spine. As illustrated, the first and second arms 952a, 952b of the connector 930 can extend proximally above the proximal surface 940p of the first portion 940 of the connector to define a second rod receiving recess 952 having a rod seat 952d that is proximal to the rod seat 920d of the receiver member 904. While the second rod-receiving recess 952 is shown as being straight, it will be appreciated that the recess can be curved or angled as described above.

Each of the arms 952a, 952b can include a feature such as a recess, dimple, notch, projection, or the like, to facilitate coupling of the connector 930 to various instruments. For example, the outer surface of each arm 952a, 952b can include an arcuate groove 954a, 954b at the respective proximal end of the arms for attaching the connector 930 to an extension tower or retractor. The arms 952a, 952b can include or can be coupled to extension or reduction tabs (not shown) that extend proximally from the connector 930 to functionally extend the length of the arms 952a, 952b. The extension tabs can facilitate insertion and reduction of a rod or other implant, as well as insertion and locking of the second set screw 934. The extension tabs can be configured to break away or otherwise be separated from the arms 952a, 952b.

The connector assembly can include various features for receiving the second rod.

Figure 10A:
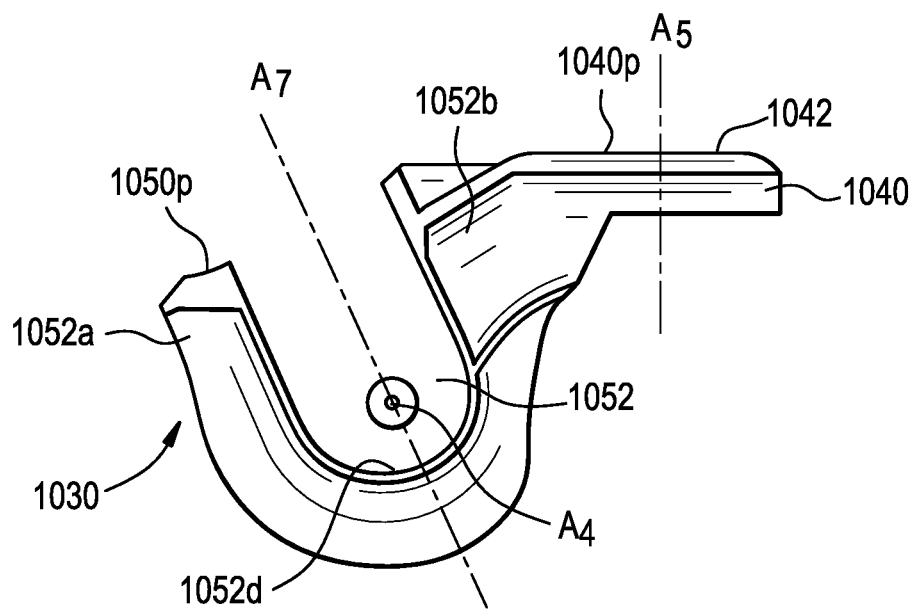
FIG. 10A is a side view of a connector having an angled rod-receiving recess.

For example, as shown in FIG. 10A, the second rod-receiving recess 1052 can have straight sidewalls instead of being curved. The second rod-receiving recess 1052 can have a central axis A7 that is obliquely angled with respect to the central axis A5 of the connector opening 1042. The arms 1052a, 1052b of the connector 1030 can define a proximal face 1050p that substantially lies in a plane perpendicular to the axis A7 and at an oblique angle relative to the proximal face 1040p of the first portion 1040 of the connector 1030. In the connector 1030 shown in FIG. 10A, the set screw is not offset from the second rod, but rather has a rotation axis that intersects the central longitudinal axis A4 of the second rod. The angled recess 1052, however, still permits the second rod to be positioned in the second seat 1052d in a close center-to-center offset relative to the first rod received in the receiver member.

Figure 10B:
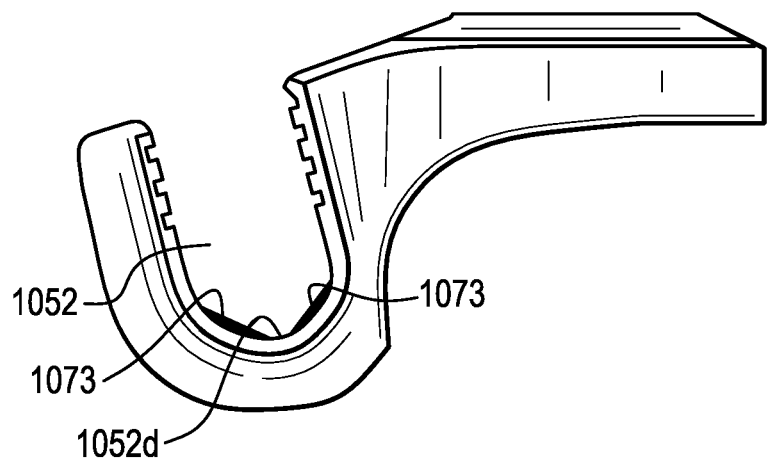
FIG. 10B is a side view of a connector having a V-shaped rod seat.

By way of further example, as shown in FIG. 10B, the second rod seat 1052d can be defined by one or more ramped or tapered surfaces. In the illustrated embodiment, the second rod seat 1052d is V-shaped with opposed planar surfaces 1073 that converge towards one another in a distal direction. A connector having this geometry can advantageously allow second rods of various different diameters to be locked securely within the recess 1052.

As noted above, the various connector features disclosed herein are interchangeable amongst the various embodiments and can be used in any combination. Any combination of the features disclosed herein are considered to be within the scope of the disclosure. Any of the connectors herein can have a second rod recess that is curved, angled, or straight. Any of the connectors herein can have a U-shaped second rod recess or a V-shaped second rod recess. Any of the connectors herein can be configured to position the second rod proximal to the first rod, distal to the first rod, or in proximal-distal alignment with the first rod. Any of the connectors herein can include a spherical articulation joint, a gimbal interface, an elongated connector opening, a uniplanar recess, or a complete locking recess. Any of the connectors herein can be configured for use with any of the positioners herein to selectively limit rotation of the connector relative to a receiver member.

An exemplary method of using the connector assemblies disclosed herein is provided below, though it will be appreciated that the connector assemblies can be used in any of a variety of other methods.

In use, referring again to FIG. 1E, a connector assembly 100 can be used to secure first and second rods 106, 107 at a surgical site within a patient. A bone anchor assembly 101 can be implanted in a bone of a patient, e.g., a first vertebra V1, using known techniques via an open procedure or a minimally-invasive procedure.

A first spinal rod 106 can be inserted into the receiver member 104 of the bone anchor assembly 101 and locked in place by tightening the first set screw 108. In some embodiments, the bone anchor assembly 101 may have been implanted in a prior procedure and the present procedure may be a revision procedure in which a tandem rod 107 is being added to an existing rod 106, in which case the existing set screw can be removed and replaced with a set screw 108 of the type described herein. In other embodiments, the bone anchor assembly 101 can be implanted as part of the same procedure as the tandem rod 107.

Before or after tightening the set screw 108, the connector 130 can be inserted over the set screw by inserting the set screw through the opening 142 of the connector. The connector 130 can be provisionally held in place by loosely coupling the nut 132 to the set screw 108.

A second spinal rod 107 can be inserted into the second rod-receiving recess 152 of the connector 130. The second rod 107 can be provisionally secured within the recess 152 by partially tightening the second set screw 134.

The connector 130, the receiver member 104, and/or the rods 106, 107 can be manipulated by the user to position the construct as desired, e.g., to obtain the desired correction. For example, the connector can be pivoted about a spherical articulation joint or gimbal interface of the type described herein. When the desired positioning is reached, the first and second set screws 108, 134 and the nut 132 can be tightened in any sequence to lock the construct. In particular, the first set screw 108 can be tightened to lock polyaxial movement of the receiver member 104 relative to the bone anchor portion 102 and to lock the first rod 106 within the receiver member 104. The second set screw 134 can be tightened to lock the second rod 107 within the connector 130. The nut 132 can be tightened to lock the relative position between the connector 130 and the receiver member 104.

The first rod 106 and/or the second rod 107 can be secured to the patient's spine using additional bone anchor assemblies, for example implanted in adjacent or nearby vertebrae, such as an adjacent vertebra V2. Multiple connector assemblies can be used to attach additional rods to the construct, or to secure the first and second rods at another position on their respective lengths to another vertebra.

The above method can be used to connect first and second rods to a vertebra using a single bone anchor. The above method can be used to connect first and second rods in tandem to achieve an offset between the first and second rods, for example to clear patient anatomy or other implants.

The connector assemblies disclosed herein and the various component parts thereof can be constructed from any of a variety of known materials. Exemplary materials include those which are suitable for use in surgical applications, including metals such as stainless steel, titanium, nickel, cobalt chromium, and combinations or alloys thereof, polymers such as PEEK, ceramics, carbon fiber, and so forth. The various components of the implants disclosed herein can be rigid or flexible. One or more components or portions of the implant can be formed from a radiopaque material to facilitate visualization under fluoroscopy and other imaging techniques, or from a radiolucent material so as not to interfere with visualization of other structures.

Exemplary radiolucent materials include carbon fiber and high-strength polymers.

The devices and methods disclosed herein can be used in minimally-invasive surgery and/or open surgery. The devices disclosed herein can be fully or partially implanted, or can be used in an external fixation system. While the devices and methods disclosed herein are generally described in the context of the spine, it will be appreciated that the methods and devices disclosed herein can be used with any human or animal bone or other tissue, in any of a variety of surgeries performed on humans or animals, and/or in fields unrelated to implants or surgery. While connectors for coupling two rods are generally disclosed herein, in some embodiments the connectors can couple three or more rods to one another. As noted above, the connector assemblies disclosed herein are not limited to use with rods, but rather can be used to couple any of a variety of different types of orthopedic devices, such as wires, tethers, plates, and the like.

Although specific embodiments are described above, it should be understood that numerous changes may be made within the spirit and scope of the concepts described. Accordingly, it is intended that this disclosure not be limited to the described embodiments.

The invention claimed is:

1. A spinal fixation method, comprising:
   implanting a bone anchor assembly in a vertebra of a patient, the bone anchor assembly including a receiver member having a first rod-receiving recess;
   inserting a first rod into the first rod-receiving recess of the receiver member;
   inserting a first fastener into the receiver member to secure the first rod in the receiver member;
   positioning a monolithic connector to directly contact the receiver member such that a proximal portion of the first fastener extends through an opening formed in the connector;
   inserting a second rod into a second rod-receiving recess formed in the connector;
   inserting a second fastener into a fastener recess formed in the connector to secure the second rod in the connector;
   adjusting an orientation of the connector relative to the receiver member to achieve a desired positioning of the first and second rods; and
   tightening a nut on the first fastener to fix the orientation of the connector relative to the receiver member.

2. The method of claim 1, further comprising positioning the first and second rods such that a ratio of a center-to-center offset, between the first and second rods, to a diameter of the first and second rods is in the range of about 2:1 to about 4:1.

3. The method of claim 1, further comprising positioning the first and second rods such that a center-to-center offset between the first and second rods is in the range of about 6 mm to about 16 mm.

4. The method of claim 1, further comprising placing a positioner between the connector and the receiver member, wherein the positioner restricts relative rotation between the connector and the receiver member about the first fastener after the nut is tightened.

5. The method of claim 1, further comprising positioning the first and second rods such that the first rod is anterior to the second rod.

6. The method of claim 1, further comprising positioning the first and second rods such that the first and second rods substantially lie in a common coronal plane.

7. The method of claim 1, wherein inserting the second rod comprises moving the second rod distally and laterally within a curved rod-receiving recess.

8. The method of claim 1, wherein inserting the second rod comprises moving the second rod distally and laterally within an obliquely angled rod-receiving recess.

9. The method of claim 1, wherein inserting the second rod comprises top loading the second rod into the connector.

10. The method of claim 1, wherein adjusting the orientation comprises pivoting the connector about at least one of a uniplanar interface, a gimbal interface, and a spherical articulation joint.

11. The method of claim 1, wherein the nut is tightened such that a portion of the nut is received within the opening.

12. A spinal fixation method, comprising:
    implanting a bone anchor assembly in a vertebra of a patient, the bone anchor assembly including a receiver member having a first rod-receiving recess;
    inserting a first rod into the first rod-receiving recess of the receiver member;
    inserting a first fastener into the receiver member to secure the first rod in the receiver member;
    positioning a connector over the receiver member such that a proximal portion of the first fastener extends through an opening formed in the connector, the connector having an inner articulation surface therein;
    tightening a nut on the first fastener to fix the orientation of the connector relative to the receiver member, the nut being received in the opening such that an outer articulation surface of the nut engages the inner articulation surface, the inner and outer articulation surfaces being complementary to one another; and
    polyaxially translating the nut relative to the connector within the opening.

13. The method of claim 12, further comprising inserting a second rod into a second rod-receiving recess formed in the connector; and inserting a second fastener into a fastener recess formed in the connector to secure the second rod in the connector.

14. The method of claim 13, further comprising adjusting an orientation of the connector relative to the receiver member to achieve a desired positioning of the first and second rods.

15. The method of claim 14, wherein the first and second rods are positioned such that the first and second rods are not parallel in any plane.

16. The method of claim 12, wherein the nut expands or contracts in a radial direction by deformation.

17. The method of claim 16, wherein the nut compresses against the inner articulation surface in the radially-expanded state to lock polyaxial movement of the connector relative to the locking nut.

18. The method of claim 16, wherein expansion in the radial direction occurs by rotating the nut relative the first fastener in a first direction and contraction in the radial direction occurs by rotating the nut relative the first fastener in a second, opposite direction.

19. The method of claim 12, further comprising engaging a proximal surface of the nut with a driver instrument to rotate the nut about the first fastener to further thread the nut onto the first fastener.

20. A spinal fixation method, comprising:
    implanting a bone anchor assembly in a vertebra of a patient, the bone anchor assembly including a receiver member having a first rod-receiving recess defined by a first pair of spaced apart arms;
    inserting a first rod into the first rod-receiving recess of the receiver member;
    inserting a monolithic first fastener into the receiver member to secure the first rod in the receiver member;
    positioning a connector over the receiver member such that a proximal portion of the monolithic first fastener extends through an opening formed in the connector;
    inserting a second rod into a second rod-receiving recess defined between a second pair of spaced apart arms formed in the connector;
    inserting a second fastener coaxially with the second rod-receiving recess between the second pair of spaced apart arms to secure the second rod in the connector;
    adjusting an orientation of the connector relative to the receiver member to achieve a desired positioning of the first and second rods; and
    tightening a nut on the monolithic first fastener to fix the orientation of the connector relative to the receiver member.

21. A spinal fixation method, comprising:
    implanting a bone anchor assembly in a vertebra of a patient, the bone anchor assembly including a receiver member having a first rod-receiving recess;
    inserting a first rod into the first rod-receiving recess of the receiver member;
    inserting a first fastener into the receiver member to secure the first rod in the receiver member;
    positioning a connector over the receiver member such that a proximal portion of the first fastener extends through an opening formed in the connector, the connector having an inner articulation surface therein; and
    tightening a nut on the first fastener to fix the orientation of the connector relative to the receiver member, the nut being received in the opening such that an outer articulation surface of the nut engages the inner articulation surface, the inner and outer articulation surfaces being complementary to one another,
    wherein the nut expands or contracts in a radial direction by deformation.

* * * * *